United States Patent
Vu et al.

(10) Patent No.: US 6,424,020 B1
(45) Date of Patent: Jul. 23, 2002

(54) HIGH DENSITY ELECTRONIC CIRCUIT MODULES

(75) Inventors: Duy-Pach Vu, Taunton; Brenda Dingle, Mansfield; Ngwe Cheong, Boston, all of MA (US)

(73) Assignee: Kopin Corporation, Taunton, MA (US)

( * ) Notice: Subject to any disclaimer, the term of this patent is extended or adjusted under 35 U.S.C. 154(b) by 0 days.

(21) Appl. No.: 08/999,352

(22) Filed: Dec. 29, 1997

Related U.S. Application Data

(60) Division of application No. 08/333,226, filed on Nov. 2, 1994, now Pat. No. 5,702,963, which is a division of application No. 07/874,588, filed on Apr. 24, 1992, now Pat. No. 5,376,561, which is a continuation-in-part of application No. 07/834,849, filed on Feb. 13, 1992, now Pat. No. 5,258,325, which is a continuation-in-part of application No. 07/636,602, filed on Dec. 31, 1990, now Pat. No. 5,206,749, and a continuation-in-part of application No. 07/643,552, filed on Jan. 18, 1991, now Pat. No. 5,300,788.

(51) Int. Cl.⁷ ............................................. H01L 29/00

(52) U.S. Cl. ...................................... 257/507; 257/685

(58) Field of Search ........................... 257/13, 507, 778, 257/685

(56) References Cited

U.S. PATENT DOCUMENTS

| | | | |
|---|---|---|---|
| 4,575,854 A | 3/1986 | Martin | 372/75 |
| 4,612,083 A | 9/1986 | Yasumoto | 156/634.1 |
| 4,727,047 A | 2/1988 | Bozler et al. | 437/89 |

(List continued on next page.)

FOREIGN PATENT DOCUMENTS

| | | |
|---|---|---|
| JP | Sho 57 106181 | 7/1982 |
| JP | 63055529 | 3/1988 |
| JP | 63-55529 | 10/1988 |
| JP | 64-38727 | 2/1989 |
| WO | WO 90/09038 | 8/1990 |
| WO | WO 91/02380 | 2/1991 |

OTHER PUBLICATIONS

Milnes, A.G., "Semiconductor Heterojunction Topics: Introduction and Overview," *Solid–State Electronics* vol.29, 2:99–121, (1986).

Akiyama, M. et al., "Growth of GaAs on Si and Its Application to FETs and LEDs," *Nat. Res. Soc. Proc.*, 67:53–64, (1986).

Turner, G. et al., "High–Speed Photoconductive Detectors Fabricated in Heteroepitaxial GaAs Layers," *Mat. Res. Soc. Symp. Proc.*, 67:181–188 (1986).

McDaniel, D.L. et al., "Vertical Cavity Surface–Emitting Semi–conductor Laser with CW Injection Laser Pumping," *IEEE Photon Technol. Lett.*, Mar. 23, 1990.

Weber, J.P. et al., "Effects of Layer Thickness Variations on Vertical Cavity Surface–Emitting DBR Semiconductor Lasers," *IEEE Photon Tech. Ltr.*, Mar. 23, 1990.

(List continued on next page.)

*Primary Examiner*—Roy Potter
(74) *Attorney, Agent, or Firm*—Hamilton, Brook, Smith & Reynolds, P.C.

(57) ABSTRACT

The invention relates to device processing, packaging and interconnects that will yield integrated electronic circuitry of higher density and complexity than can be obtained by using conventional multi-chip modules. Processes include the formation of complex multi-function circuitry on common module substrates using circuit tiles of silicon thin-films which are transferred, interconnected and packaged. Circuit modules using integrated transfer/interconnect processes compatible with extremely high density and complexity provide large-area active-matrix displays with on-board drivers and logic in a complete glass-based modules. Other applications are contemplated, such as, displays, microprocessor and memory devices, and communication circuits with optical input and output.

37 Claims, 25 Drawing Sheets

U.S. PATENT DOCUMENTS

| | | | | |
|---|---|---|---|---|
| 4,769,680 A | | 9/1988 | Resor, III et al. | 355/43 |
| 4,774,205 A | | 9/1988 | Choi et al. | 437/59 |
| 4,846,931 A | | 7/1989 | Gmitter et al. | 156/633 |
| 4,855,255 A | | 8/1989 | Goodhue | 456/633 |
| 4,863,877 A | | 9/1989 | Fan et al. | 437/22 |
| 4,870,475 A | | 9/1989 | Endo et al. | 357/71 |
| 4,878,098 A | * | 10/1989 | Saito et al. | 257/778 |
| 4,883,561 A | | 11/1989 | Gmitter et al. | 156/633 |
| 4,935,792 A | | 6/1990 | Tanaka et al. | 357/23.7 |
| 4,961,629 A | | 10/1990 | Kato | 350/332 |
| 4,979,002 A | | 12/1990 | Pankove | 357/17 |
| 5,045,895 A | | 9/1991 | Yoshida et al. | 357/17 |
| 5,073,806 A | | 12/1991 | Idei | 357/17 |
| 5,087,585 A | | 2/1992 | Hayashi | 437/915 |
| 5,670,826 A | * | 9/1997 | Bessho et al. | 257/778 |
| 5,841,197 A | * | 11/1998 | Adamic, Jr. | 257/507 |
| 5,998,232 A | * | 12/1999 | Maruska | 257/13 |

OTHER PUBLICATIONS

"3–D Chip–On–Chip Stacking," *Semiconductor International*, Dec. 1991.

McClelland et al., "A Technique for Producing Epitaxial Films on Reusable Substrates", *Appl. Phys. Lett.*37, 560, Sep. 15, 1980.

Yablonovitch et al., "Extreme Selectivity in the Lift–off of Epitaxial GaAs Films," *Appl. Phys. Lett.*51, 2222 Dec. 28, 1987.

Fan et al., "Lateral Epitaxy by Seeded Solidification for Growth of Crystal Si Films on Insulators," *Appl. Phys. Lett.*38, 365, Mar. 1, 1981.

Allen et al., "Characterization of Isolated Silicon Epitaxy Material," SPIE vol. 945—Advanced Processing of Semiconductor Devices II (3/17–3/18, 1988).

Conference Record of the 1991 International Display Research Conference, (Oct. 15–17, 1991) IEEE.

Y. Hayashi et al., "A New Three Dimensional IC Fabrication Technology, Stacking This Film Dual–CMOS Layers," 1991 IEEE IEDM, pp. 657–660.

U. Konig, "Dreidimensionale Integration," Electroniker, (10):79–82 (Oct. 1989). (English translation only).

E. Hofmeister, "Mikroelektronik 2000," Siemans Components, 27(2):54–58 (Mar./Apr. 1989). (English Translation Only).

* cited by examiner

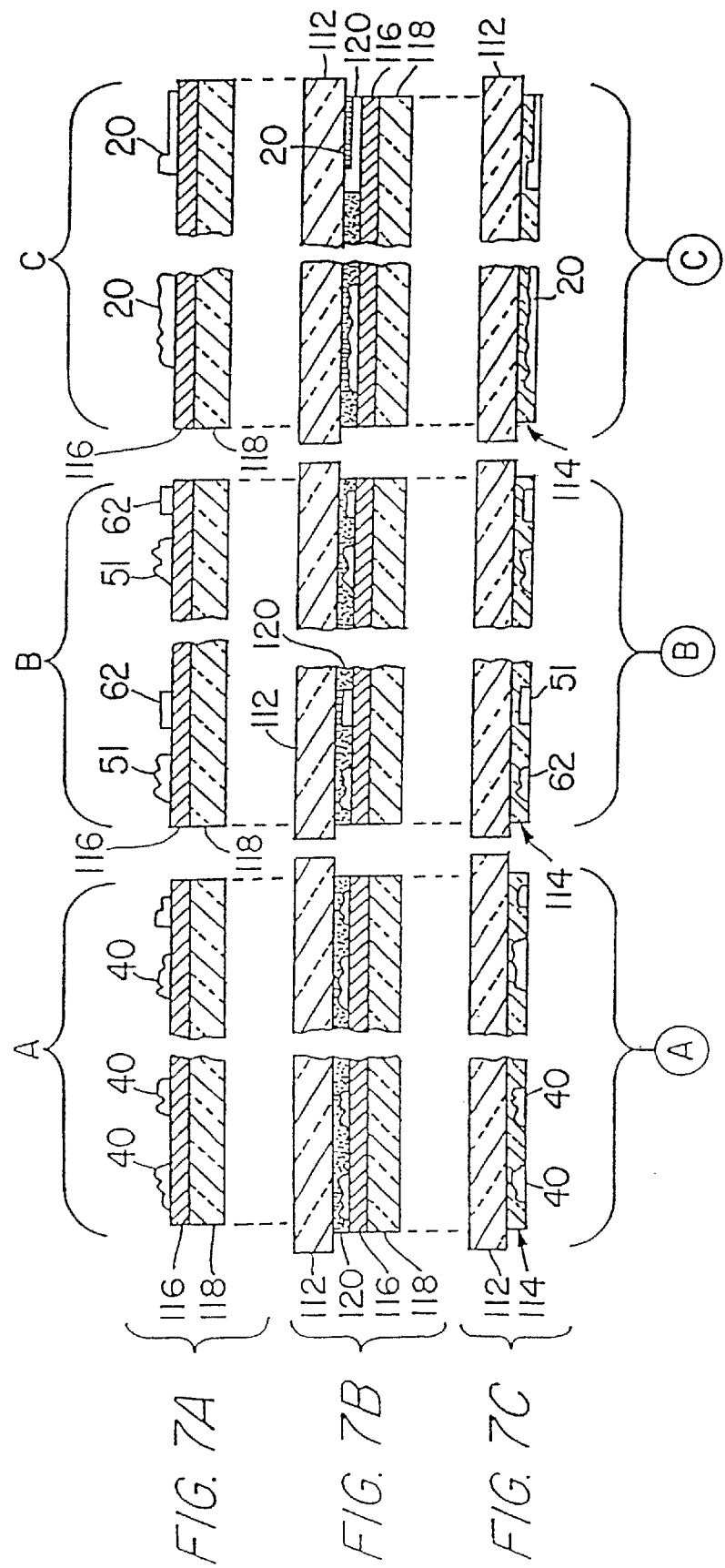

HIGH DENSITY ELECTRONIC CIRCUIT MODULES

This is a divisional of U.S. Ser. No. 08/333,226 now U.S. Pat. No. 5,702,963 filed Nov. 2, 1994, which is a divisional of U.S. Ser. No. 07/874,588 now U.S. Pat. No. 5,376,561 filed Apr. 24, 1992 which is a continuation-in-part of U.S. Ser. No. 07/834,849 now U.S. Pat. No. 5,258,325 filed Feb. 13, 1992 which is a continuation-in-part of U.S. Ser. No. 07/636,602 filed Dec. 31, 1990 now U.S. Pat. No. 5,206,749 and U.S. Ser. No. 07/643,552 filed Jan. 18, 1991 now U.S. Pat. No. 5,300,788.

BACKGROUND OF THE INVENTION

The development of new portable electronic products, such as the laptop computer, is currently of great worldwide interest. Miniaturization of the various component systems (memories, displays, and so forth) for such products requires that the necessary circuits be packed in as small a volume as possible. Packing circuits into a small volume also reduces parasitic capacitance and improves signal propagation time between circuits. One approach to this requirement is to increase the scale of integration in order to obtain all of the required functions from a circuit made from a single wafer. Unfortunately, efforts to create full-wafer circuitry have encountered unacceptable yield losses owing to the large circuit size. In the specific area of active matrix displays, a similar problem results in attempting the scale-up of the display size to and beyond the 256 K pixel level.

Active matrix (AM) displays generally consist of flat-panels consisting of liquid crystals or electroluminescent materials which are switched "on" and "off" by electric fields emanating from pixel electrodes charged by thin-film transistors (TFT's) co-located with each liquid crystal or electroluminescent pixel area. These AM displays are expected to supplant cathode ray tube (CRT) technology and provide a more highly defined television picture or data display. The primary advantage of the active matrix approach, using TFT's, is the elimination of cross-talk between pixels, and the excellent grey scale that can be attained with TFT-compatible liquid crystal displays (LCD's).

Flat panel displays employing LCD's generally include five different layers: a white light source layer, a first polarizing filter layer that is mounted on one side of a circuit panel on which the TFT's are arrayed to form pixels, a filter plate layer containing at least three primary colors arranged into pixels, and finally a second polarizing filter layer. A volume between the circuit panel and the filter plate is filled with a liquid crystal material. This material rotates the polarization of light passing through it when an appropriate electric field is applied across it. Thus, when a particular pixel electrode of the display is charged up by an associated TFT, the liquid crystal material rotates polarized light being transmitted through the material so that it will pass through the second polarizing filter and be seen by the viewer.

The primary approach to TFT formation over the large areas required for flat panel displays has involved the use of films of amorphous silicon which has previously been developed for large-area photovoltaic devices. Although the TFT approach has proven to be feasible, the use of amorphous silicon compromises certain aspects of the panel performance. For example, amorphous silicon TFT's lack the frequency response needed for large area displays due to the low electron mobility inherent in amorphous material. Thus, the use of amorphous silicon limits display speed, and is also unsuitable for the fast logic needed to drive the display.

Owing to the limitations of amorphous silicon, other alternative materials are being considered, such as, polycrystalline silicon, or laser recrystallized silicon. Thin films, less than about 0.4 microns, of these materials are usually formed on glass which generally restricts further circuit processing to low temperatures.

The formation of large active-matrix displays is hampered by the unavailability of large-area single crystal Si material. Thus the conventional approach is to use thin-film amorphous ($\alpha$-Si) or polycrystalline Si (poly-Si) wafers. The required number of thin-film transistors (TFT's), combined with the large number of driver circuits and the thin-film material defects inherent in $\alpha$-Si or poly-Si, leads to unacceptable yield and quality problems when the entire display is to be fabricated as a unit.

A need exists, therefore, for a relatively inexpensive way to reliably form hybrid high density electronic circuits, including active matrices, memories, and other devices, in a modular approach that permits small high-quality parts or circuits to be assembled into complete large-area high-quality complex devices.

SUMMARY OF THE INVENTION

The present invention comprises a method, and resulting apparatus, for fabricating complex hybrid multi-function circuitry a common module body, such as a substrate or superstrate, by using silicon thin film transfer processes to remove areas or tiles of circuits, formed in Si thin-films, and transferring, locating and adhering the removed tiles to a common module body. The removal of areas or tiles is hereinafter referred to, generally, as "dicing." The process of transferring, locating and adhering is generally referred to as "tiling."

The films may be formed of $\alpha$-Si, poly-Si, or x-Si depending upon the desired circuit parameters. Elements of one circuit are then interconnected to elements of another circuit by conventional photolithographically patterned thin film metallization techniques. Direct laser writing or erasing may be used for repair or modification of interconnects.

The transfer may be accomplished in either of two ways—single transfer or double transfer. In the single transfer process, the desired Si circuitry is formed on a thin film Si substrate; the Si circuits are diced, i.e., divided into dice or tiles containing one or more circuits; the dice or tiles are then tiled, i.e., sequentially registered onto a common module body and sequentially adhered to the module body. After all the dice or tiles are adhered, all the Si substrates are removed in one process and the circuits interconnected. Alternately, the Si substrates may be sequentially removed if more precise alignment is required.

In the double transfer process, the circuits are transferred to an intermediary transfer or carrier body and then the substrates are removed. Dicing may occur before or after the first transferral. The thin film circuitry is supported by the transfer body until transfer to the common module body is appropriate. The circuitry is then tiled, i.e., sequentially transferred, registered and adhered to the common module body. If the transfer body is sufficiently thin, the transfer body may be left on the circuitry. If not, it is removed and circuit interconnections made, as required.

In a preferred embodiment, the common module forms an active matrix (AM) LCD panel fabricated in accordance with the invention. The circuit panel for the AMLCD is formed by transferring to a common module substrate or superstrate, multiple x-Si and/or $\alpha$-Si or poly-Si thin film tiles upon which circuits may have been formed, and wherein each tile is obtained as a unit from one or more wafers. During transfer, the tiles are registered with respect to one another. Circuits are then interconnected as necessary. Registration is accomplished by well-known X-Y micropositioning equipment. Adherence and planarity are achieved using optically transparent adhesives which fill in voids left in forming circuitry. Trimming of substrate edges may be required to obtain precise circuit dimensions needed for proper alignment on the module body.

Other preferred embodiments of the present invention relate to the formation of three-dimensional circuits and devices. Significantly, these three dimensional circuits and devices provide for high density circuitry in small areas. As such, three-dimensional (3-D) circuits and devices can be used to fabricate high density electronic circuitry including stacked memories, multi-functional parallel processing circuits, high density low-power CMOS static RAMs, peripheral drive circuitry for display panels and a plurality of high-speed low-power CMOS devices.

In accordance with the present invention, a preferred fabrication process comprises single and double transfer of silicon films and backside processing of said films for providing various 3-D circuits and devices. In one preferred embodiment, a 3-D double gate MOSFET device can be fabricated. First, a standard MOSFET having drain, source and gate regions is formed in a silicon layer of an SOI structure by any suitable technique. Next, the MOSFET is single transferred to a superstrate for backside processing. A region of the insulating layer is removed to expose a backside region of the silicon layer. A second gate is then formed adjacent the backside region of the silicon layer opposite the first gate. A conductive contact is attached to the second gate, thereby providing a 3-D double gate MOSFET.

In another embodiment of the present invention, a 3-D double gate MOSFET inverter is fabricated such that its n-channel MOSFET and its p-channel MOSFET share the same body with their respective channels disposed on opposite sides of the shared body. In fabricating this inverter, a silicon layer is formed over an insulating layer on a substrate. After the silicon is patterned into an island, a series of doping steps are performed on the silicon to produce a first MOSFET having a first drain, a first source and channel region (which is a portion of the shared body region). The first drain, first source and channel regions are disposed along a first axis in a plane extending through the silicon. Another series of doping steps are subsequently performed on the silicon to produce a second MOSFET having a second drain, a second source and a channel region which are disposed along a second axis extending perpendicular to the first axis. A first gate is then formed on one side of the plane of the silicon, and contacts are attached to the first source, first drain, first gate, second source and second drain. The silicon is bonded to a superstrate and the substrate is removed for backside processing. Accordingly, a region of the insulating layer is removed to exposed a backside region of the silicon island and a second gate is formed. The second gate is positioned on the opposite side of the plane of the silicon island as the first gate over the channel region. A contact is then attached to the second gate and the two gates can then be electrically connected.

In another embodiment, another 3-D double gate MOSFET inverter is formed of a pair of vertically stacked MOSFETs. The fabrication sequence involves forming a first MOSFET device in a first silicon layer over a first substrate, and a second MOSFET device in a second silicon layer over a second substrate. The first MOSFET device is transferred to a superstrate, and the second MOSFET device is transferred to a optically transmissive substrate. Next, the first silicon layer is stacked onto the second silicon layer such that the two MOSFET devices are vertically aligned. The MOSFETs are then electrically interconnected to provide an 3-D inverter circuit.

In yet another embodiment, a vertical bipolar transistor is fabricated in accordance with the principles of the invention. The fabrication process begins with providing a silicon layer over an insulating layer on a substrate. Next, a series of doping steps are performed to produce a collector region, an emitter region and a base region. Conductive contacts are then formed for the collector, emitter and base. The structure can be single transferred to a superstrate for backside processing. To that end, a region of the insulating layer is removed to expose a backside region of the silicon layer. A metal layer is applied over the exposed backside of the silicon and sintered.

BRIEF DESCRIPTION OF THE DRAWINGS

FIGS. 7A and 7D are a process flow sequence illustrating transfer and bonding of a silicon on oxide (SOI) structure to a glass superstrate and removal of the substrate.

DETAILS DESCRIPTION OF THE INVENTION

I. Tiled Active Matrix Liquid Crystal Display

Figure 1:
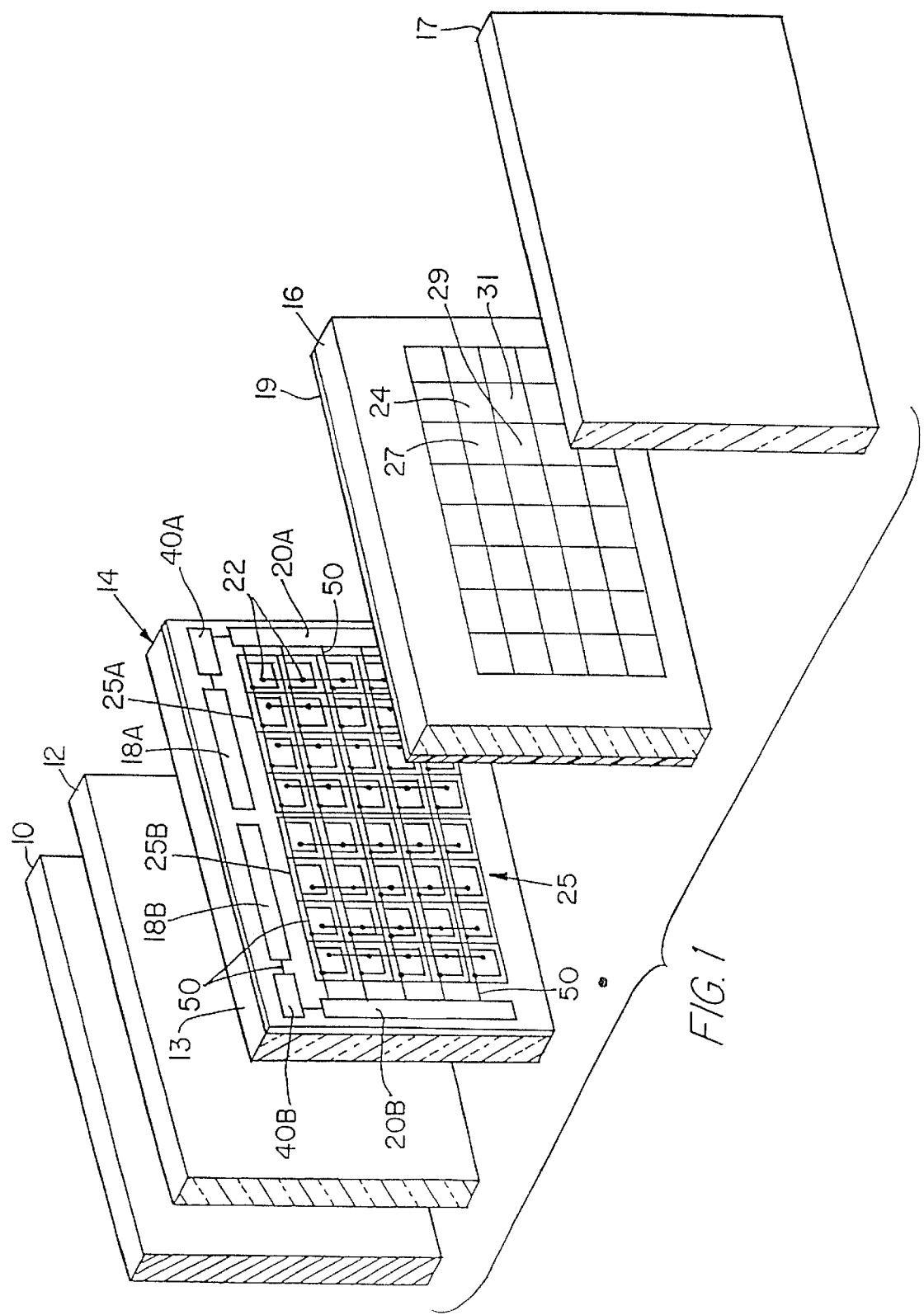
FIG. 1 is a perspective view of a high density circuit module in the form of an active matrix liquid crystal display (AMLDC).

A preferred embodiment of the invention for fabricating complex hybrid multi-function circuitry on common module substrates is illustrated in the context of an AMLCD, as shown in FIG. 1. The basic components of the AMLCD comprise a light source 10, such as a flat fluorescent or incandescent white lamp, or an electroluminescent lamp having white, or red, blue and green phosphors, a first polarizing filter 12, a circuit panel 14, an optional filter plate 16 and a second polarizing filter 17, which form a layered structure. Note: Filter plate 16 is not needed for a black and white display or where the red, green and blue colors are provided by the lamp at the appropriate pixel. A liquid crystal material 23, such as a twisted nematic is placed between the circuit panel 14 and the filter plate 16.

Figure 2A:
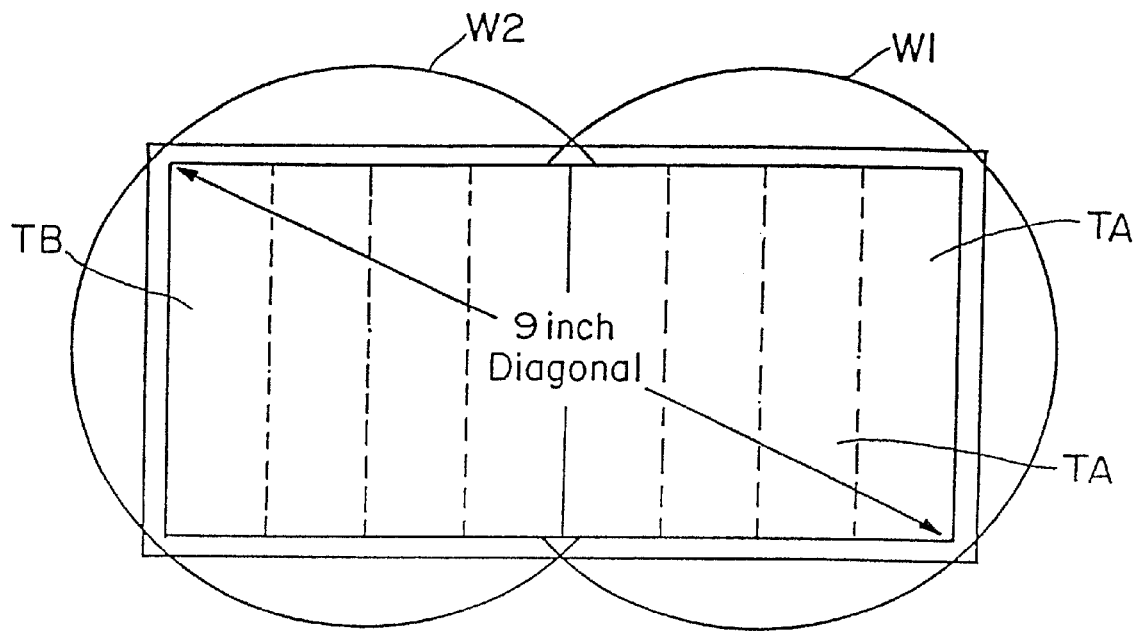
FIG. 2A is a schematic illustrating how two six inch wafers can be used to form tiles for a 4×8 inch AMLDC.
Figure 2B:
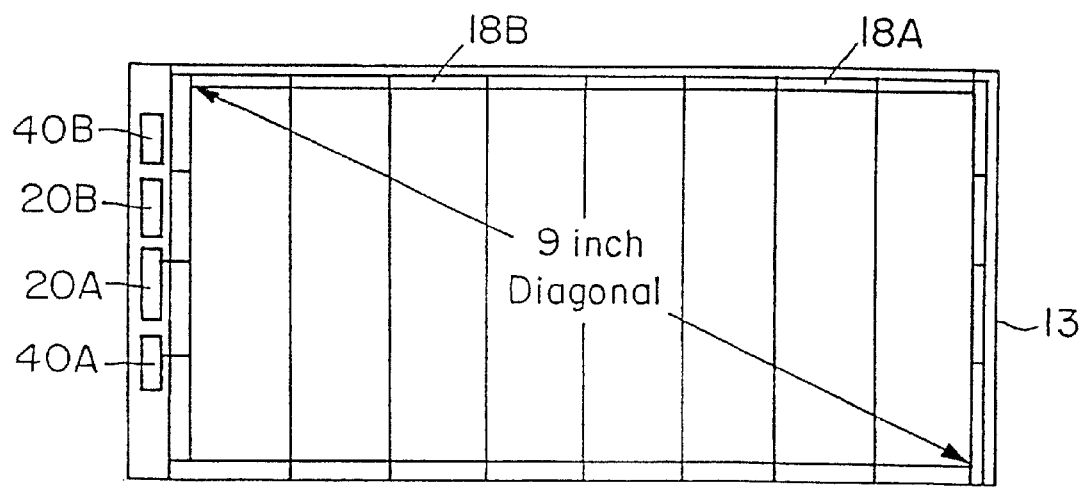
FIG. 2B shows the tiles of FIG. 2A applied to a glass substrate for forming an AMLDC.

Circuit panel 14 consists of a transparent common module body 13 formed, for example, of glass upon which is transferred a plurality of common multifunction circuits comprising control logic circuits 40A and 40B and drive circuits 18A and 18B, 20A and 20B, and array circuit 25A and 25B. Preferably, the logic and drive circuits which require high speed operation are formed in tiles of x-si. The array circuits may be formed in α-Si material, or poly-Si, or preferably in x-Si, to achieve lower leakage in the resultant TFT's and, hence, better grey scale. Higher speed is also achieved in x-Si. A 4×8 inch active matrix LCD array can be formed from two standard 6-inch diameter Si wafers W1 and W2 as shown in FIG. 2A. Array circuit 25A is formed on wafer W1 and 1-inch by 4-inch tiles TA are transferred from the wafer W1 to the substrate 14. Note: The transfer may be accomplished using either a single or double transfer process, as will be described in detail below. Each tile is registered against another using micropositioning equipment and manipulators capable of micron scale accuracy. Similarly, tiles TB are transferred from wafer W2 to form array 25B on substrate or common module body 13 (See FIG. 2B).

Logic circuits 40A and 40B and drive circuits 18A, 18B, 20A, 20B are formed on other suitable substrates (not shown) and tiled and transferred in like manner to common substrate 13 and registered opposite the arrays 25A, 25B, as shown in FIG. 1. Conductive interconnections 50 are then made between the drive circuits and the individual pixels 22 and the logic control circuits 40A and 40B. In this manner, a 1280 by 1024 addressable array of pixels 22 are formed on the substrate 13 of circuit panel 14. Each pixel 22 is actuated by voltage from a respective drive circuit 18A or B on the X-axis and 20A or B on the Y-axis. The X and Y drive circuits are controlled by signals from control logic circuits 40A and B. Each pixel 19 produces an electric field in the liquid crystal material 23 disposed between the pixel and a counterelectrode (not shown) formed on the back side of the color filter plate 16.

The electric field formed by pixels 22 causes a rotation of the polarization of light being transmitted across the liquid crystal material that results in an adjacent color filter element being illuminated. The color filters of filter plate system 16 are arranged into groups of four filter elements, such as blue 24, green 31, red 27, and white 29. The pixels associated with filter elements can be selectively actuated to provide any desired color for that pixel group.

Figure 3:
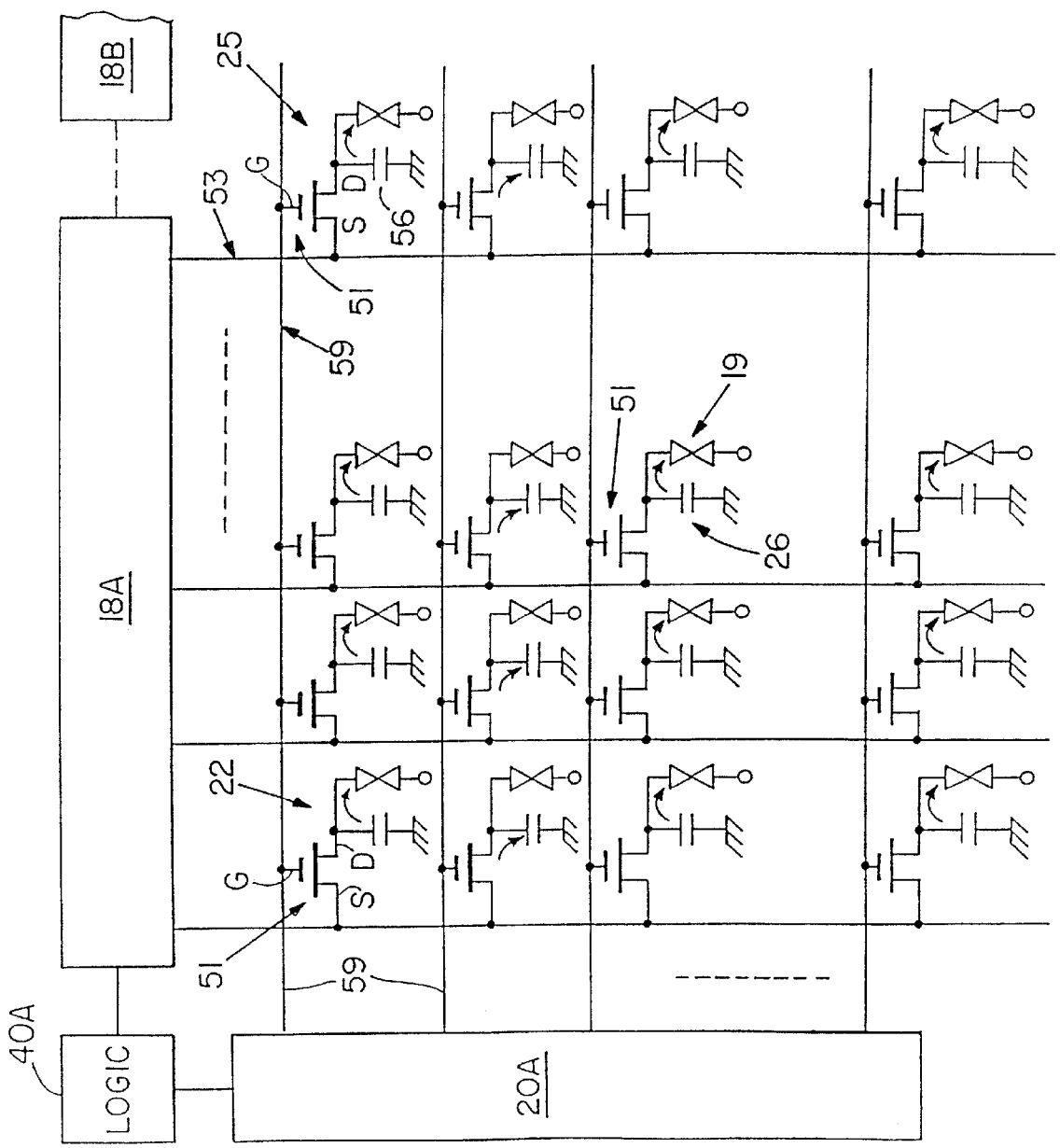
FIG. 3 is a circuit diagram illustrating the driver system for the AMLDC of FIG. 1.

A typical drive and logic circuit that can be used to control the array pixels 22 is illustrated in FIG. 3. Drive circuit 18A receives an incoming signal from control logic 40A and sends a signal to each source electrode of a TFT 51 in one of the columns selected by logic circuit 40A through interconnect line 53. Y-drive circuit 20A controlled by logic circuit 40A energizes a row buss 59 extending perpendicular to column buss 53 and applies a voltage pulse to each gate G of TFT's 51 in a selected row. When a TFT has a voltage pulse on both its gate and source electrode current flows through an individual transistor 51, which charges capacitor 56 in a respective pixel 22. The capacitor 56 sustains a charge on the pixel electrode adjacent to the liquid crystal material (shown schematically at 19) until the next scan of the pixel array 25. Note: The various embodiments of the invention may, or may not, utilize capacitors 56 with each pixel depending upon the type of display desired.

II. Transfer Processes

The array circuits 25A and 25B and logic 40A, 40B and drive circuits 18A, 18B may be formed and transferred by a number of processes. The basic steps in a single transfer process are: forming of a plurality of thin film Si circuits on Si substrates, dicing the thin film to form tiles, and transferring the tiles to a common module substrate by "tiling." Tiling involves the steps of transferring, registering the transferred tiles, and adhering the registered tiles. The Si substrates are then removed and the circuits on the tiles are interconnected.

The double transfer approach, described in detail below in connection with FIGS. 4A–4L is similar except that the Si-substrate is removed after dicing and the thin film is transferred to an intermediate transfer body or carrier before ultimate transfer to the common module body.

Assuming an Isolated Silicon Epitaxy (ISE) process is used, the first step is to form a thin-film precursor structure of silicon-on-insulator (SOI) film. An SOI structure, such as that shown in FIG. 4A, includes a substrate 32 of Si, a buffer layer 30, of semi-insulating Si and an oxide 34 (such as, for example, $SiO_2$) that is grown or deposited on buffer layer 30, usually by Chemical Vapor Deposition (CVD). An optional release layer 36 of material which etches slower than the underlying oxide layer 34 is then formed over the oxide 34.

For example, a silicon oxy-nitride release layer, comprising a mixture of silicon nitride ($S_3N_4$) and silicon dioxide ($SiO_2$) may be a suitable choice. Such a layer etches more slowly in hydrofluoric acid than does $SiO_2$ alone. This etch rate can be controlled by adjusting the ratio of N and O in the silicon oxy-nitride ($SiO_xN_y$) compound.

A thin essentially single crystal layer 38 of silicon is then formed over the release layer 36. The oxide (or insulator) 34 is thus buried beneath the Si surface layer. For the case of ISE SOI structures, the top layer is essentially single-crystal recrystallized silicon, from which CMOS circuits can be fabricated.

Note: for the purposes of the present application, the term "essentially" single crystal means a film in which a majority of crystals show a common crystalline orientation and extend over a cross-sectional area in a plane of the film for at least 0.1 $cm^2$, and preferably, in the range of 0.5–1.0 $cm^2$, or more. The term also includes completely single crystal Si.

The use of a buried insulator provides devices having higher speeds than can be obtained in conventional bulk (Czochralski) material. Circuits containing in excess of 1.5 million CMOS transistors have been successfully fabricated in ISE material. An optional capping layer (not shown) also of silicon nitride may also be formed over layer 36 and removed when active devices are formed.

Figure 4A:
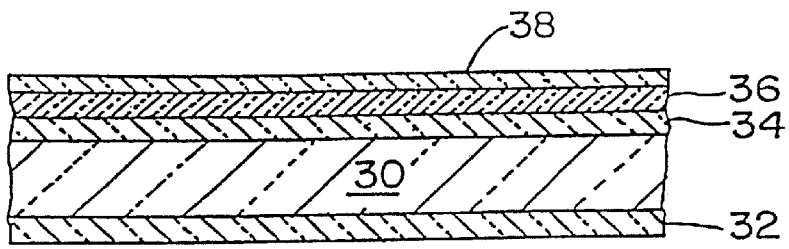
FIGS. 4A–4L is a preferred process flow sequence illustrating the fabrication of the a portion of the circuit panel for the AMLDC of FIG. 1.
Figure 4B:
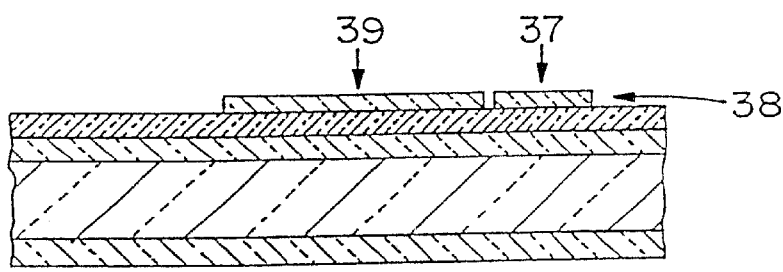
Figure 4C:
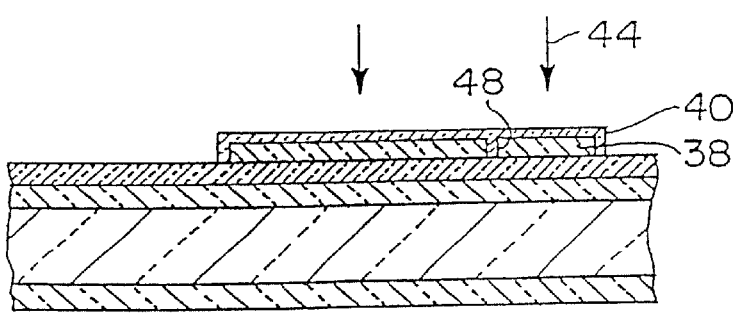

As shown in FIG. 4B, the film 38 is patterned to define active circuits, such as a TFT's in region 37 and a pixel electrode region at 39 for each display pixel. Note: For simplification, only one TFT 51 and one pixel electrode 62 is illustrated (FIG. 4H). It should be understood that an array of 1280 by 1024 such elements can in practice be formed on a single 6-inch wafer.

A plurality of arrays may be formed on a single six-inch wafer, which are then applied to the display as tiles and interconnected. Alternatively, the plurality of pixel matrices from one wafer can be separated and used in different displays. The plurality may comprise one large rectangular array surrounded by several smaller arrays (to be used in smaller displays). By mixing rectangular arrays of different areas, such an arrangement makes better use of the total available area on a round wafer.

An oxide layer 40 is then formed over the patterned regions including an insulator region 48 formed between the two regions 37, 39 of each pixel. The intrinsic crystallized material 38 is then implanted 44 (at FIG. 4C) with boron or other p-type dopants to provide a n-channel device (or alternatively, an n-type dopant for a p-channel device).

Figure 4D:
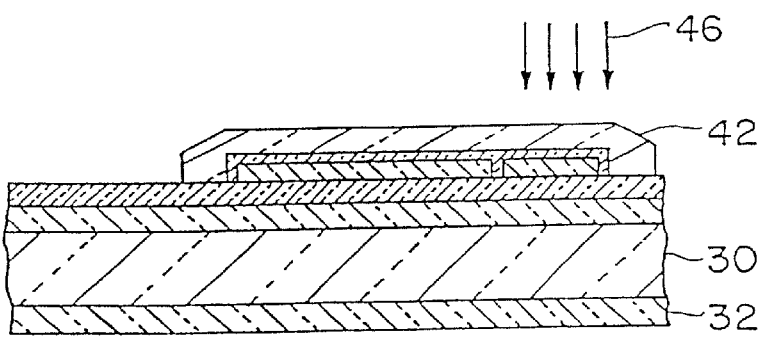
Figure 4E:
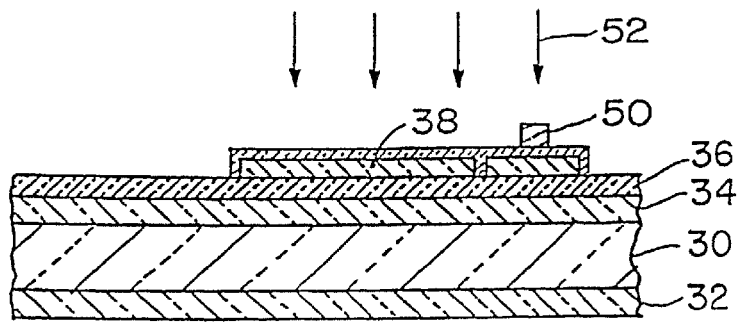
Figure 4F:
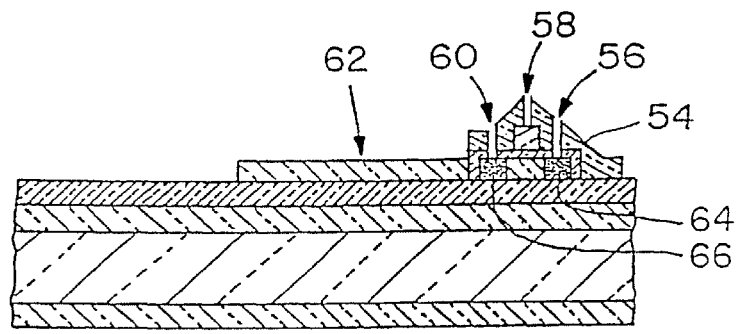
Figure 4G:
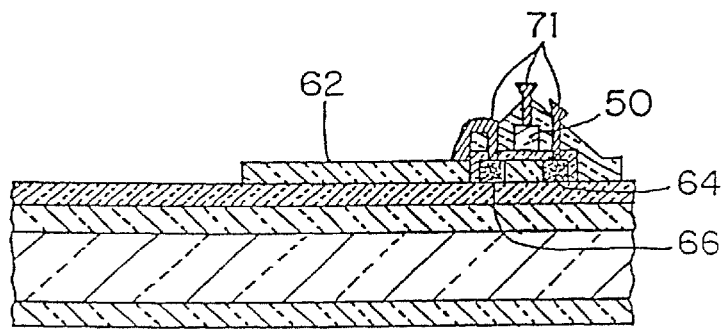
Figure 4H:
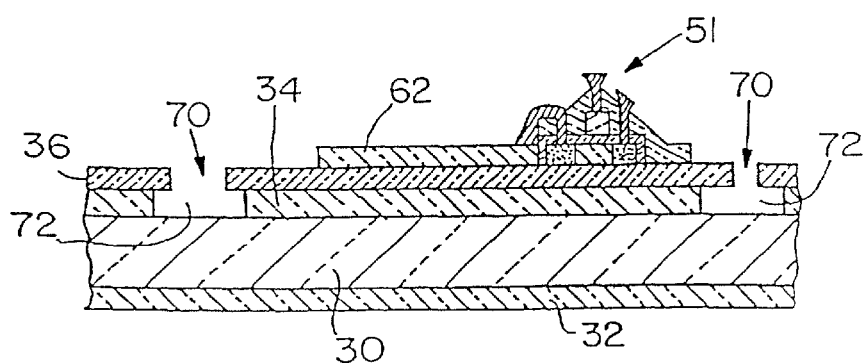

A polycrystalline silicon layer 42 is then deposited over the pixel and the layer 42 is then implanted 46, through a mask as seen in FIG. 4D, with an n-type dopant to lower the resistivity of the layer 42 to be used as the gate of the TFT. Next, the polysilicon 42 is patterned to form a gate 50, as seen in FIG. 4E, which is followed by a large implant 52 of boron to provide p+ source and drain regions 66, 64 for the TFT on either side of the gate electrode. As shown in FIG. 4F, an oxide 54 is formed over the transistor and openings 60, 56, 58 are formed through the oxide 54 to contact the source 66, the drain 64, and the gate 50. A patterned metallization 71 of aluminum, tungsten or other suitable metal is used to connect the exposed pixel electrode 62 to the source 66 (or drain), and to connect the gate and drain to other circuit panel components.

The devices have now been processed and the circuits may now be tested and repaired, as required, before further processing occurs.

The next step in the process is to transfer the silicon pixel circuit film to a common module, either directly, or by a double transfer from substrate to carrier and then to the common module. A double transfer approach is illustrated in FIGS. 4H–4L. To separate a circuit tile from the buffer 30 and substrate 37, a first opening 70 (in FIG. 4H) is etched in an exposed region of release layer 36 that occurs between tiles. Oxide layer 34 etches more rapidly in HF than nitride layer 36, thus a larger portion of layer 34 is removed to form cavity 72. A portion of layer 36 thus extends over the cavity 72.

Figure 4I:
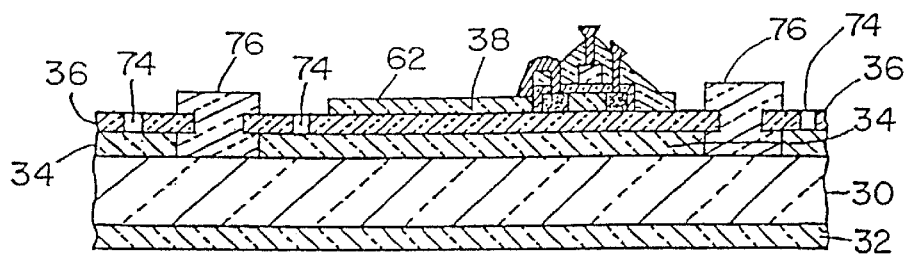
Figure 4J:
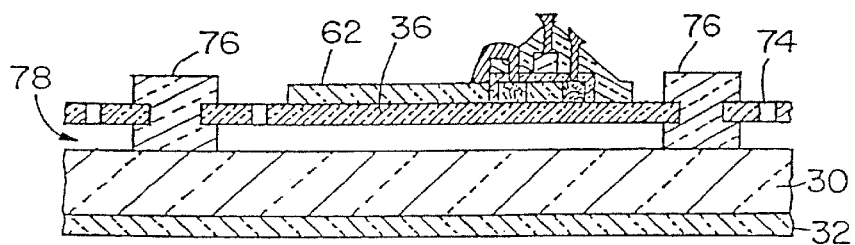
Figure 4K:
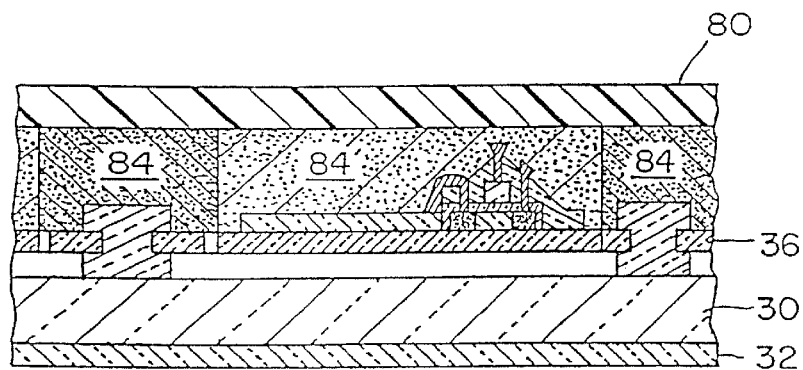
Figure 4L:
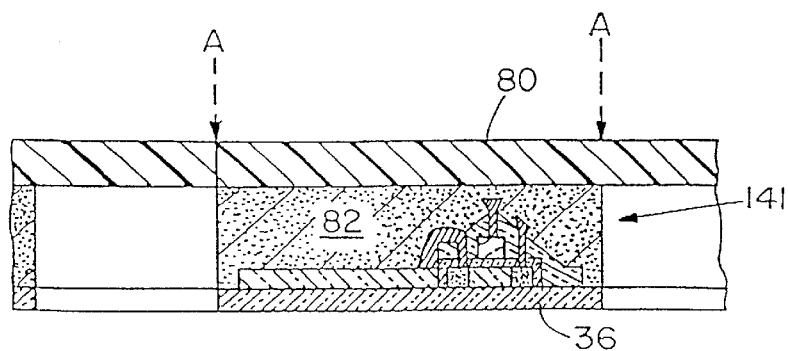

In FIG. 4I, a support post 76 of oxide is formed to fill cavity 72 and opening 70, which extends over a portion of layer 36. Openings or via holes 74 are then provided through layer 36 such that an etchant can be introduced through holes 74, or through openings 78 etched beneath the release layer 36, to remove layer 34 (See FIG. 4J). The remaining release layer 36 and the circuitry supported thereon is now held in place relative to substrate 32 and buffer 30 with support posts 76.

Next, an epoxy 84 that can be cured with ultraviolet light is used to attach an optically transmissive superstrate 80 to the circuitry, and layer 36. The buffer 30 and substrate 32 is then patterned and selectively exposed to light such that regions of epoxy 84' about the posts 76 remain uncured while the remaining epoxy 84' is cured (See FIG. 4K). The buffer 30 and substrate 32 and posts 76 are removed by cleavage of the oxide post and dissolution of the uncured 84 epoxy to provide the thin film tile structure 141, shown in FIG. 4L mounted on carrier 80.

To form the final display panel, the edges of the carrier 80 are trimmed to coincide with the tile borders. The nitride release layer 36 is removed by etching.

Figure 5A:
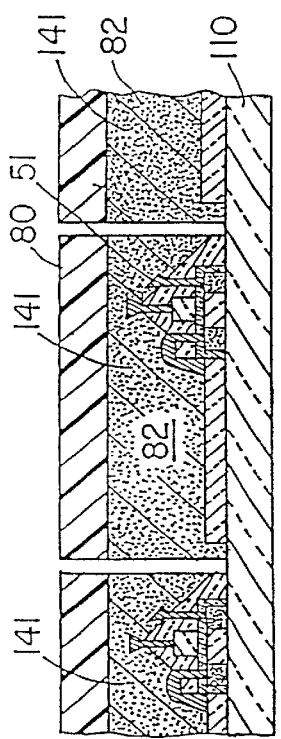
FIGS. 5A and 5B are cross-sectional schematic process views of a portion of the AMLDC.
Figure 5B:
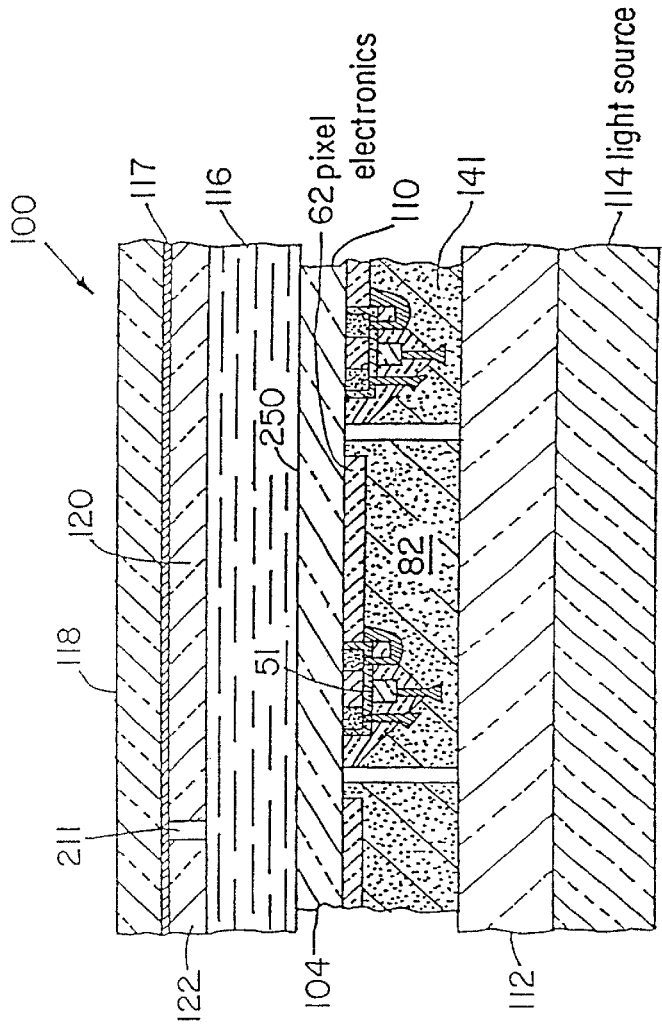

As shown in FIG. 5A, a plurality of tile structures 141 are then sequentially registered with one another and adhered to a common module body 110 using a suitable adhesive (not shown). Common module body 110 is preferably patterned with interconnect metallization on the surface facing the tile structure 141 for interconnecting individual tile circuitry with each other. Next, insulation and alignment layers, spacers, a sealing border and bonding pads for connections (not shown) are bonded onto the periphery of the common module body 110. A screen printing process can be used to prepare the border. As shown in FIG. 5B, a plate 117 containing the color filters 120 and the counterelectrode (not shown) is bonded to the periphery thin film circuit tiles 141 with the sealing border after insertion of spacers (not shown). The display is filled with the selected liquid crystal material 116 via a small filling hole or holes extending through the border. This filling hole is then sealed with a resin or epoxy. First and second polarizer films 118, 112 or layers are then bonded to both sides and connectors (not shown) are added. Finally, a white light source 114, or other suitable light source, is bonded to polarizer 112.

Pixel electrodes 62 are laterally spaced from each other. Each pixel has a transistor 51 and a color filter 120 or 122 associated therewith. A bonding element or adhesive 82 and optically transmissive superstrate 110, such as glass or plastic completes the structure. Body 110 is preferably a low temperature glass that can have a thickness preferably of about 200 to 1000 microns.

In an alternative CLEFT process, thin single-crystal films, are grown by chemical vapor deposition (CVD), and separated from a reusable homoepitaxial substrate.

The films removed from the substrate by CLEFT are "essentially" single-crystal, of low defect density, are only a few microns thick, and consequently, circuit panels formed by this process have little weight and good light transmission characteristics.

The CLEFT process, illustrated in U.S. Pat. No. 4,727,047, involves the following steps: growth of the desired thin film over a release layer (a plane of weakness), formation of metallization and other coatings, formation of a bond between the film and a second substrate, such as glass (or superstrate), and separation along the built-in-plane of weakness by cleaving. The substrate is then available for reuse.

The CLEFT process is used to form sheets of essentially single crystal material using lateral epitaxial growth to form a continuous film on top of a release layer. For silicon, the lateral epitaxy is accomplished either by selective CVD or, preferably, the ISE process or other recrystallization procedures. Alternatively, other standard deposition techniques can be used to form the necessary thin film of essentially single crystal material.

One of the necessary properties of the material that forms the release layer is the lack of adhesion between the layer and the semiconductor film. When a weak plane has been created by the release layer, the film can be cleaved from the substrate without any degradation. As noted in connection with FIGS. 4A–4C, the release layers can comprise multilayer films of $Si_3N_4$ and $SiO_2$. Such an approach permits the $SiO_2$ to be used to passivate the back of the CMOS logic. (The $Si_3N_4$ is the layer that is dissolved to produce the plane of weakness.) In the CLEFT approach, the circuits are first bonded to the glass, or other transfer substrate, and then separated, resulting in simpler handling as compared to, for example, UV-cured tape.

In the ISE process, the oxide film is strongly attached to the substrate and to the top Si film which will contain the circuits. For this reason, it is necessary to reduce the strength of the bond chemically. This requires use of a release layer that is preferentially dissolved with an etchant without complete separation to form a plane of weakness in the release layer. The films can then be separated mechanically after the glass is bonded to the circuits and electrodes.

Mechanical separation may be accomplished by bonding the upper surface of the Si film to a superstrate, such as glass, using a transparent epoxy. The film and glass are then bonded with wax to glass plates about 5 mm thick that serve as cleaving supports. A metal wedge is inserted between the two glass plates to force the surfaces apart. Since the mask has low adhesion to the substrate, the film is cleaved from the substrate but remains mounted on the glass. The substrate can then be used for another cycle of the CLEFT process, and the device processing may then be completed on the back surface of the film. Note that since the device remains attached to a superstrate, the back side can be subjected to standard wafer processing, including photolithography.

Figure 6:
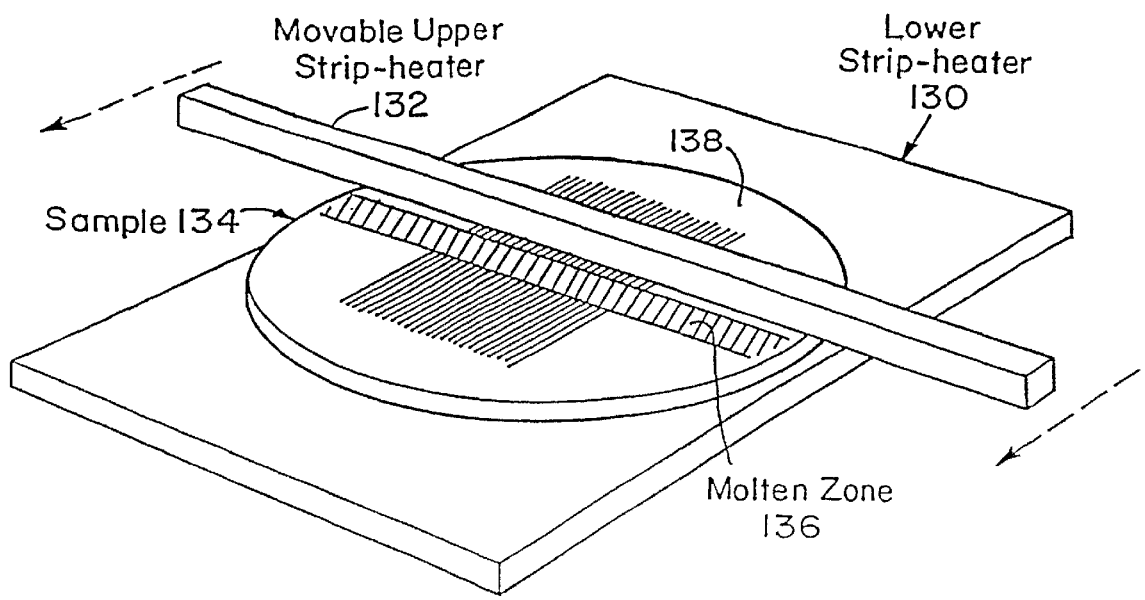
FIG. 6 illustrates in a perspective view a preferred embodiment of a system used for recrystallization.

One embodiment of the invention utilizes a recrystallization system, shown schematically in FIG. 6 to form the essentially single crystal Si thin film. A sample wafer 134 is formed of poly Si, formed on $SiO_2$, formed on an Si wafer. A capping layer 138 is formed over the poly Si. The wafer temperature is then elevated to near the melting point by a lower heater 130. An upper wire or graphite strip heater 132 is then scanned across the top of the sample 134 to cause a moving melt zone 136 to recrystallize or further crystallize the polycrystalline silicon. The lateral epitaxy is seeded from small openings formed through the lower oxide. The resultant single crystal film has the orientation of the substrate.

III. Alternate Adhesion and Transfer Processes

Figure 7D:
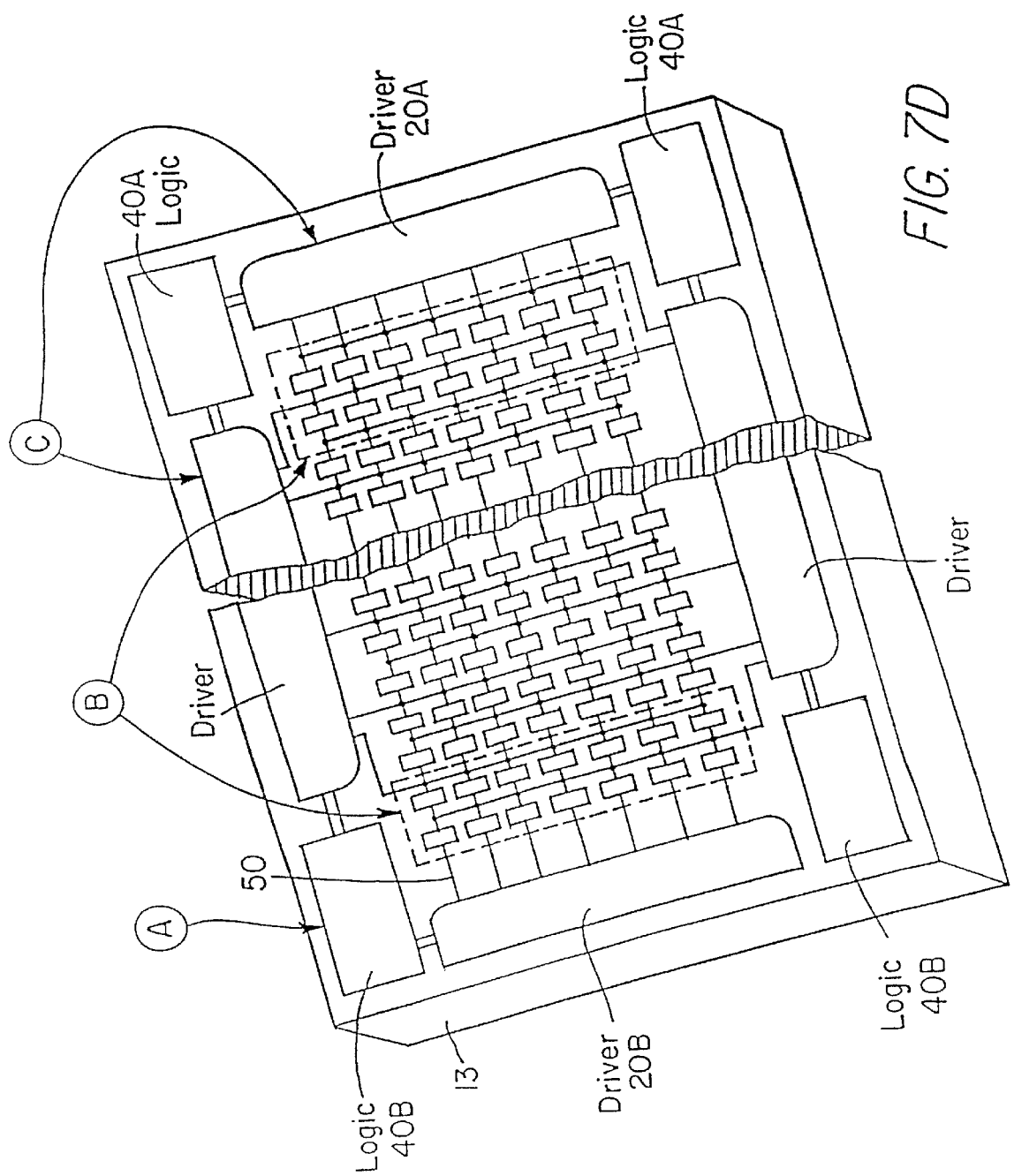

FIGS. 7A and 7D illustrate an alternate preferred double transfer process for adhering and transferring tiles of circuits of thin films of silicon to a common module body. The starting structure is a silicon wafer 118 upon which an oxide layer 116 and a thin film of poly-Si, α-Si or x-Si 114 is formed using any of the previously described processes such as ISE or CLEFT. A plurality of circuits, such as pixel electrodes, TFT's, Si drivers and Si logic circuits, are then formed in the thin film. FIG. 7A shows three such wafers, I, II, III. In wafer I, logic circuits 40 are formed. In wafer II, pixel electrodes 62 and TFT's 51 are formed. In wafer III, driver circuits 20 are formed. A wafer, or individual tiles diced from the wafer, is attached to a superstrate transfer body 112, such as glass or other transparent insulator, using an adhesive 120. Preferably the adhesive is comprised of an epoxy, such as, a cycloaliphatic anhydride; for example, EP-112 made by Masterbond Inc. The adhesive must satisfy the following criteria:

Excellent spectral transmission in the visible range;
Good adhesion to glass, oxides, metals, nitrides;
No reactions with glass, metals, oxides, nitrides;
Low shrinkage;
Low warp/stress;
Able to tolerate acids at 100 C. for extended periods without lifting, losing adhesion, or degrading;
Able to withstand 180° C. for 2 hours with no optical change;
Good resistance to acids and solvents;
Able to tolerate dicing and heating steps (including an acid etch step with no lifting);
Low viscosity to allow thin adhesive films; and
Ability to be vacuum degassed to eliminate all bubbles.

In general,, the cycloaliphatic anhydrides meet most of the above criteria. The epoxy preferably has a low cure temperature to minimize shrinkage, a very low ion content (<5 ppm) and spectral stability over extended time periods.

The wafer, or tile, 230 is attached, using the adhesive 120, to a glass superstrate 112. The adhesive is vacuum degassed to eliminate all bubbles. The sandwich structure is then cured at a low temperature of about 100° C. for 4–8 hours which causes the adhesive to gel and minimizes the shrinkage characteristics. Then the adhesive is fully cured at a higher temperature of about 160° C. for about 8 hours. This cure assures that the bonds are fully matured. Without this cure, the adhesive will not stand up to the subsequent acid etching step.

The wafer, or tile, is then cleaned and the native oxide 118 is etched off the back surface. The wafer is put into a solution (KOH or equivalent) of 25 grams to 75 ml $H_2O$ at 100° C. Depending on the thickness of the wafer, it may take up to 5 hours to etch the Si 118 and oxide 116 layers. The solution etches silicon very rapidly, i.e. 2 to 3 microns/min., and uniformly if the wafers are held horizontally in the solution with the etching surface face up. The acid has a very low etch rate on oxide, so that as the substrate is etched away and the buried oxide is exposed, the etching rate goes down. The selectivity of the silicon etch rate in KOH versus the oxide etch rate in KOH is very high (200:1). This selectivity, combined with the uniformity of the silicon etching, allows the observer to monitor the process and to stop the etch in the buried oxide layer 116' without punching through to the thin silicon layer 114 above it. Wafers up to 25 mils thick and oxides as thin as 4000 Å have been successfully etched using this process. An alternative etchant is hydrazine, which has a much higher etch rate selectivity or ethylene diamine pyrocatacol (EDP).

When the silicon is completely gone, the vigorous bubbling, which is characteristic of silicon etching in KOH, abruptly stops, signalling that the etching is complete.

The thin films 114 transferred to the respective glass superstrates 112 are now rinsed and dried. If not already provided with circuits 40, 51, 62 or 20, the films 114 can be backside circuit processed, if desired, since the epoxy adhesive 120 has very good resistance to chemicals. In addition, the epoxy is very low in stress, so that the thin film is very flat. and can go through conventional photolithography steps.

After all the necessary circuits are formed, as above, on transfer bodies 112, they may now be diced and tiled onto a common module body 13 to perform a combined function, such as an AMLCD.

The logic circuits 40 of transfer body 118 in col. A, FIG. 7C, are transferred to the border of module body 13, while the driver circuits 20 from the transfer body 118 in col. C, FIG. 7C, are disposed on the border between the logic circuits 40A and 40B.

Tiles of pixel electrodes 62 and TFT's 51 are formed by dicing or etching and are registered with respect to each other and pre-formed wiring 50 on module body 13, as shown.

After all the circuits are registered and adhered to the module body, the transfer body 118 and the epoxy 120 is removed using a suitable etchant, such as HF for the case of a glass transfer body.

Interconnection of circuits is achieved during registration or by direct laser writing where necessary. Also, if desired, the film can be transferred to another substrate and the first glass superstrate and adhesive can be etched off, allowing access to the front side of the wafer for further circuit processing.

Figure 8A:
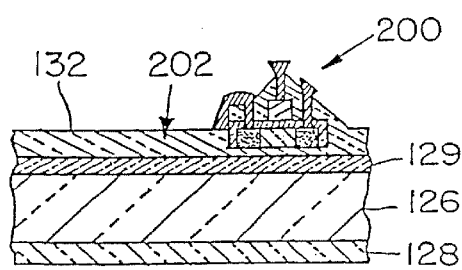
FIGS. 8A and 8B is a process flow sequence illustrating an alternative transfer process in which a GeSi alloy is used as an intermediate etch step layer.
Figure 8B:
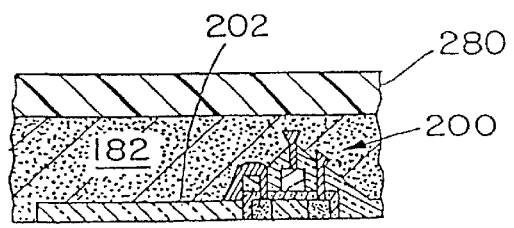

FIGS. 8A and 8B illustrate an alternative one-step silicon thin film transfer process in which GeSi is used as an intermediate etch stop layer. In this process, Si buffer layer 126 is formed on an x-Si substrate 128 followed by a thin GeSi layer 129 and a thin α-Si, poly-Si, or x-Si device or circuit layer 132; using well-known CVD or MBE growth systems.

The layer 132 is then IC processed in the manner previously described in connection with FIGS. 4E–H, to form circuits, such as TFT's 200 and pixel electrodes 202 (FIG. 8A). Next, the processed wafers, or tiles from the wafer, are mounted on a common module glass (or other) support 280 using an epoxy adhesive of the type previously mentioned in connection with FIGS. 7A–7B. The epoxy fills in the voids formed by the previous processing and adheres the front face to the superstrate 280.

Next, the original Si substrate 128 and Si buffer 126 are removed by etching with a KOH solution, which does not affect the GeSi layer 129 (FIGS. 8B). Finally, the GeSi layer 124 is removed by brief submersion in a suitable etch.

V. Pressure Sensor Embodiment

Figure 9A:
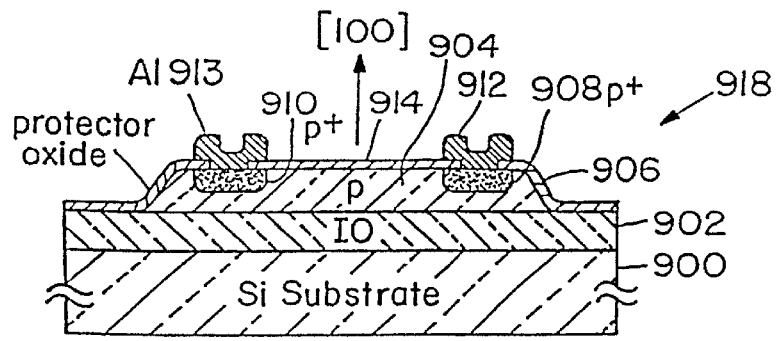
FIGS. 9A and 9B is a process flow sequence illustrating another thin film tile isolate and transfer process used to form a pressure sensor or an array of such sensors.
Figure 9B:
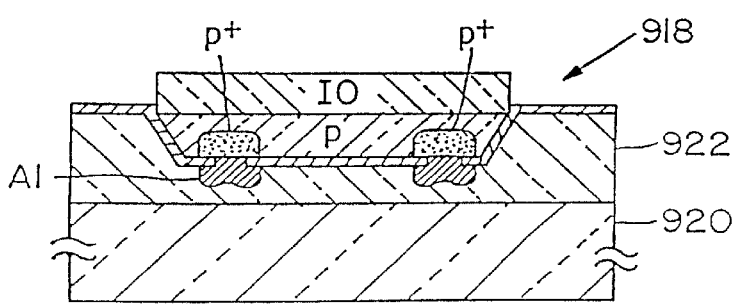

FIGS. 9A–9B illustrate an alternate embodiment related to isolating and transferring circuits. In a representative embodiment, a method of fabricating pressure sensing transducers on a glass substrate is shown in FIGS. 9A–9B and described hereinafter. The transducer circuit operates by sensing a change in the resistance of the p-region 904 in response to pressure applied to the circuit. This resistance change may be sensed by an ohmmeter coupled across contacts 912 and 912 and calibrated and converted into a pressure sensor to serve as a strain gauge. The starting structure is shown in FIG. 9A. An SOI wafer is provided which consists of an Si substrate 900 beneath a buried oxide layer 902, upon which is formed a single, or nearly single, crystal Si layer 904. A blanket implant of boron ions is made to make the Si layer a p-type conductor. A thin (1000 Å) blanket protective/mask layer of oxide ($SiO_2$) (not shown) is then formed over the structure. (Note FIG. 9A shows the structure after processing). Single, or nearly single, islands of x-Si are then formed by applying photo-resist over the oxide structure and etching the oxide and silicon 904 between islands to align the edges of the islands parallel to the [110] plane. Photo resist is applied again and contact openings formed to contact regions 910 and 908, which are then implanted with a high dose of boron ions to form $P^+$ type conductivity regions. A protective oxide layer 906 is then formed over the island. Aluminum contact pads, 912 and 913 to the contacts 908, 910 are formed in openings provided through oxide 906. The pressure transducer circuit of FIG. 9A is now ready for transfer to a temporary glass substrate.

After the circuit 918 is formed, the circuit is transferred to a temporary substrate 920 using a removable epoxy 922. The silicon substrate 900 is etched away in a KOH solution. Then using a photoresist and mask the initial oxide layer 902 is etched around the periphery of the circuit 918 leaving the circuit free to be inverted and transferred to the glass substrate 920 and releasibly bonded thereto using the removable epoxy 922 from which it can be transferred and bonded to a module for general sensing, including temperature, pressure, acceleration, and so forth, all under microprocessor supervision, to make a high speed process controller.

Figure 10A:
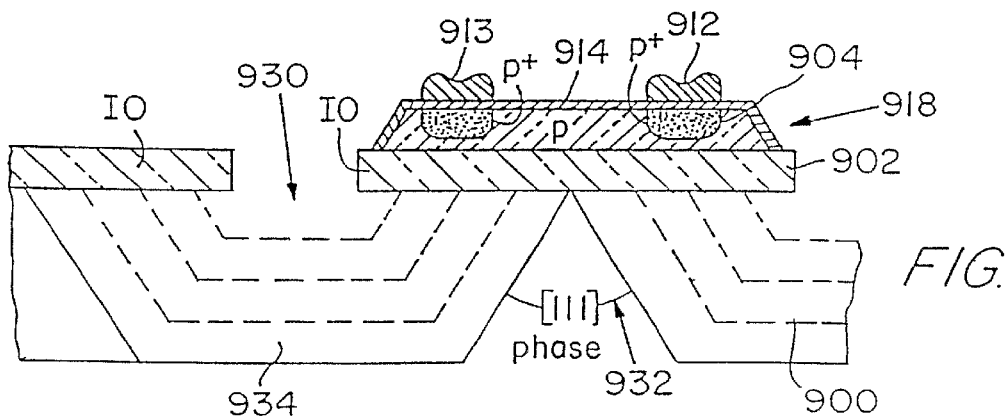
FIGS. 10A and 10B illustrate an alternate process to the process of FIGS. 9A and 9B.
Figure 10B:
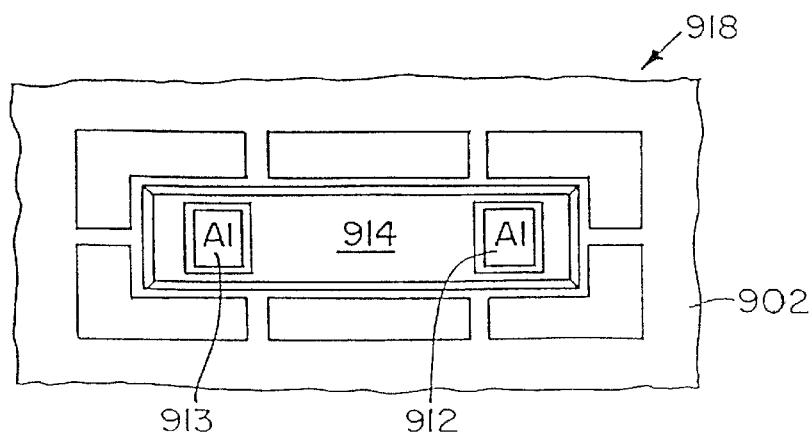

FIGS. 10A and 10B illustrate an alternate transfer process in which the initial oxide 902 is etched about the periphery of each circuit 918 using a conventional photo-resist and mask technique. The Si substrate 900 is also etched locally using hydrazine which preferentially etches Si to reveal the [111] plane. A nitride layer may be added such that the hydrazine does not etch the aluminum. Etching of the Si substrate with hydrazine undercuts the circuits 918 forming a cavity 930 under the circuits and leaving a bridge structure 934 between circuits 918 and the substrate.

When it is desired to remove one or more circuits 918, a vacuum wand may be used to seize one or more circuits and break the bridge to remove the circuits which may then be transferred along with other circuits to a common module substrate and aligned and interconnected with other circuitry to perform an overall function as previously described. Alternatively, other techniques such as laser ablation can be used for removing the circuits from the substrate.

FIG. 10B is a top-plan view of FIG. 10A before substrate 900 is etched where the bridges 934 are shown. The bridges make an angle of about 22° relative to the long symmetry axis of the circuit 918.

VIII. Three-Dimensional Circuitry

A) 3-D Circuit Architecture

Figure 11A:
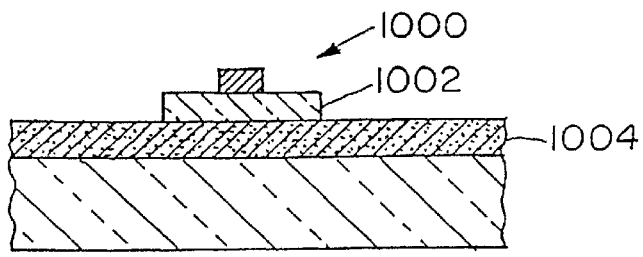
FIGS. 11A–11D is a process flow sequence illustrating circuit transfer steps employed in the formation of a three-dimensional circuit.
Figure 11B:
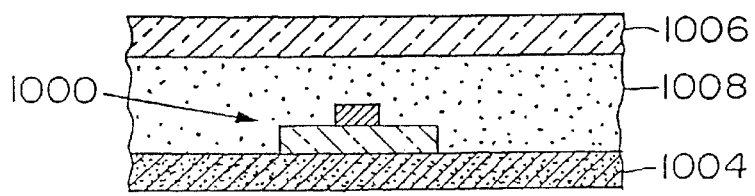
Figure 11C:
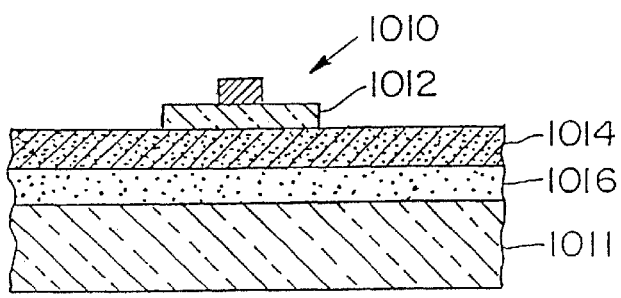

Other embodiments of the present invention relate to the formation of three-dimensional circuits. In forming a two-layer three-dimensional circuit, a first circuit 1000 (FIG. 11A) formed in a silicon layer 1002 on an oxide layer 1004 on an Si substrate 1006 is transferred onto a glass superstrate 1006 as shown in FIG. 11B. More specifically, the single-transferred circuit 1000 is transferred to a glass superstrate, coated with amorphous silicon, by any of the aforementioned transfer methods and bonded to the glass with an adhesive or epoxy 1008. Referring to FIG. 11C, a second circuit 1010 is double-transferred to a glass substrate 1011. The circuit 1010 is preferably formed in a layer of silicon 1012 on an oxide layer 1014, and is bonded to the substrate by a layer of adhesive or epoxy 1016.

Figure 11D:
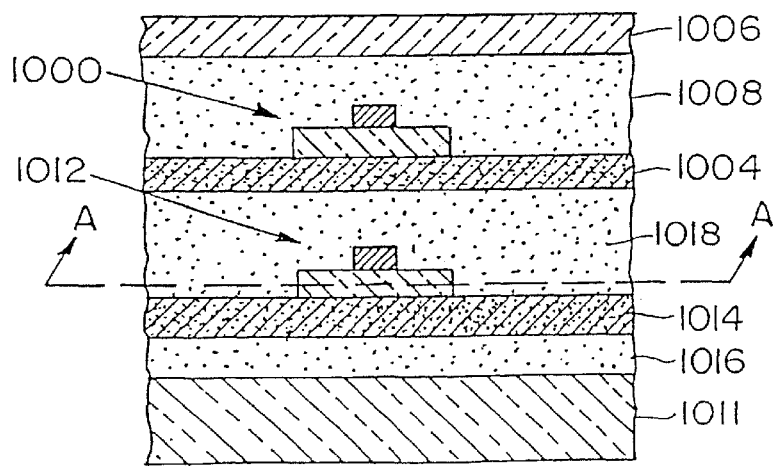

Referring to FIG. 11D, a three-dimensional device is formed by bonding the single-transferred circuit 1000 (FIG. 11B) on top of the double-transferred circuit 1010 (FIG. 11C) using thin, uniform adhesive 1018. Since the circuits can be observed through the glass substrate 1011, they can be aligned using a microscope or a contact proximity aligner as routinely done in photolithography where a mask is aligned on top of a silicon circuit in process or by other appropriate micropositioning tools or techniques.

After bonding, the superstrate 1006 is removed as in a double-transfer process and the adhesive 1008 is removed in oxygen plasma. This leaves the front surface of the top circuit 1000 exposed. The bottom circuit 1010 is buried beneath the adhesive layer 1018. In order to make. connections between the layers of circuits, openings or via holes (not shown) are defined by appropriate etchants in order to expose contact areas on the two circuit layers. All of the oxide is etched in buffered HF using photoresist as a mask while the adhesive can be etched in oxygen plasma or by reactive ion etching (RIE) using the previously etched oxide as a mask. Once these via holes have been opened in the bonding layer, they can be filled with metal in order to make the contact from layer to layer. The layer to layer interconnections are explained in detail below. The adhesive layer between the superposed circuits must be kept very thin, a few microns thick for the layer to layer contacting to be possible. The process can be repeated to add additional layers to the device.

Figure 12A:
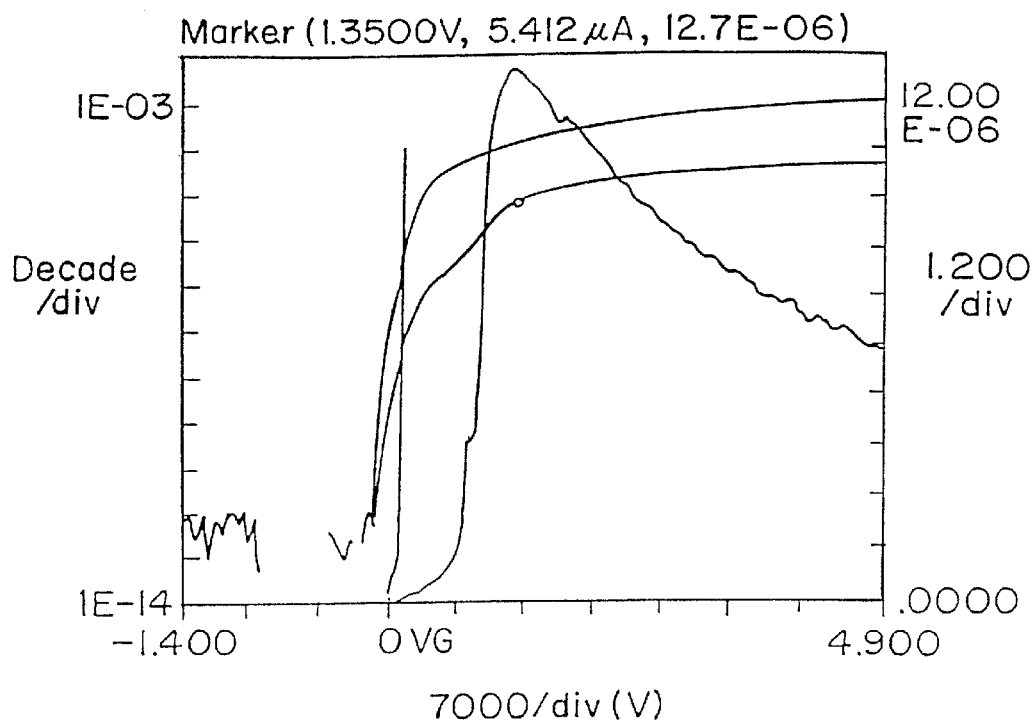
FIGS. 12A–12B are graphs illustrating the drive current and transconductance of a MOSFET circuit surrounded by an adhesive and positioned on a glass substrate and a MOSFET circuit surrounded by air and positioned on a glass substrate respectively.
Figure 12B:
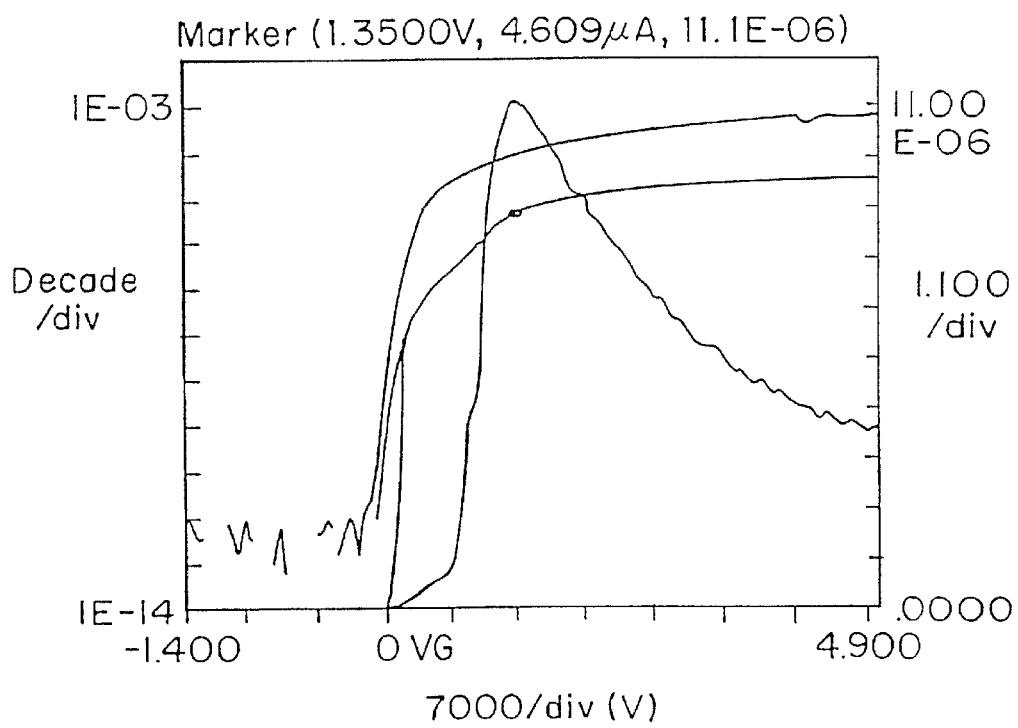

The performance characteristics of each circuit in a three-dimensional structure are related to the conductivity of the medium in which the circuit is disposed. FIGS. 12A–12B show performance curves of a lower MOSFET circuit of a three-dimensional device (such as in FIG. 11D) and the corresponding curves for a similar device after double-transfer and before three-dimensional mounting (such as in FIG. 11C). The graphs of FIGS. 12 A–12B show that the transconductance and the drive current are higher when the circuit is buried under epoxy (FIG. 11D) than when it is exposed to ambient air (FIG. 11C). This effect can be explained by the 5.4 times higher thermal conductivity of the epoxy with respect to air which results in a reduced heating effect for the circuit buried in epoxy (FIG. 11D). It is noted that carrier mobility decreases as the temperature of the circuit increases and that performance is directly related to carrier mobility. Thus, surrounding circuits in highly conductive epoxies provide lower device temperatures leading to improved performance characteristics. Table I compares the thermal conductivities of a few of the many different materials that can be used:

TABLE I

| Material | $\lambda(W)\ (m^{-1})\ (°K^{-1})$ |
|---|---|
| Si | 150 |
| $SiO_2$ | 1.4 |
| Air* | 0.024 |
| Ep112 | 0.13 |

*Not including free convection

There are many available thermally conductive/electrically insulating epoxies. Castall, Tracon, Masterbond, and Epotek all make a number of versions of heat conductive epoxies. The highest conductivities are achieved by filling an epoxy resin with various materials including alumina and aluminum nitride. Hitachi also makes a diamond filled epoxy. All the alumina and aluminum nitride filled epoxies are opaque due to the conductive particles used as fillers. They can be cured at room temperature or at elevated temperatures. The aluminum nitride filled epoxies have thermal conductivities of ~3.6 $(W^{-1})\ (m^{-1})\ (°K^{-1})$. Aluminum oxide filled epoxies are in the 1.44–21.6 range. Diamond filled epoxies are the best of all. These filled epoxies can be made to accommodate temperatures up to 250° C. The aluminum nitride particle size is 5 $\mu$m or greater. Aluminum oxide particle size can be made much smaller so thinner bondlines are possible. Some trade names are Masterbond EP21, Supreme 10, Tracon 2151, Castall E340 series, Epotek H62, H70E. Also, silicon carbide filled epoxies can be used.

It is noted that the filled epoxies sampled are generally viscous, opaque pastes such that it may be difficult to obtain very thin (<5 $\mu$m) bondlines. Medium thermal conductance in the 0.85–1.44 (W) $(m^{-1})\ (°K^{-1})$ range can be achieved without fillers. These epoxies are of slightly lower viscosity, can be put on thinner and are preferable if the conductance is high enough. Another option is to coat the devices with a thin diamond like film or a conductive ceramic like aluminum nitride to facilitate heat removal. This decreases the thermal conductance criteria for the epoxy, allowing the use of a lower viscosity epoxy in order to achieve the thin bondlines necessary for layer to layer interconnections.

Figure 13A:
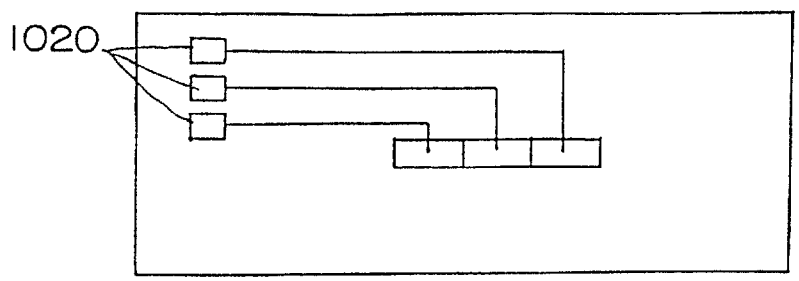
FIGS. 13A–13B is a process flow sequence illustrating the formation of electrical interconnections between layered devices.
Figure 13B:
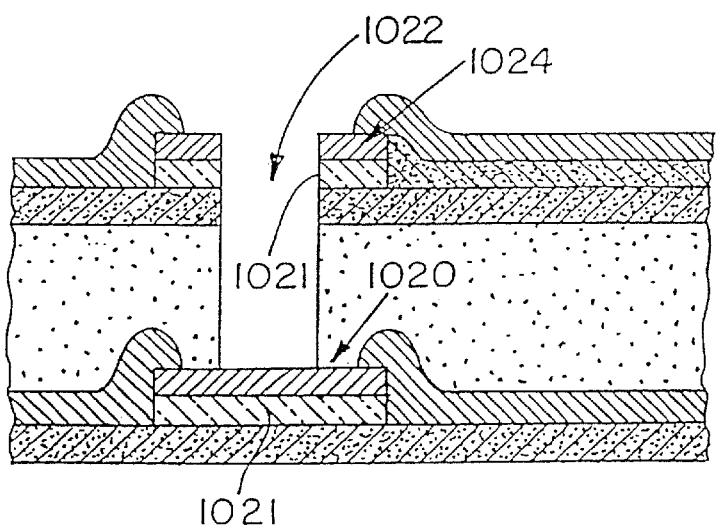

One significant aspect in the formation of three-dimensional circuits involves interconnecting the layered devices. It is noted that in such circuits, the epoxy disposed between the device layers may be spun to obtain a thickness of a few microns. Alternatively, other known techniques can be employed to obtain a thin, uniform layers of epoxy. FIG. 13A is a sectional view of FIG. 11D taken along the line A—A and shows the lower contact area 1020 formed via metalization in the plane of the silicon layer 1012 for providing electrical connection to the circuit 1010 (FIG. 11D). Similarly, upper contact areas (not shown) are formed directly above the lower areas in the plane of the silicon layer 1002 and are electrically connected to the upper circuit 1000 (FIG. 11D). Referring to FIG. 13B, the upper and lower areas (1024, 1020) employ an optional poly-Si layer for strengthening the areas for contacts. Via holes 1022 are formed through the upper contact areas 1024 to gain access to the lower contact areas 1020. The etching to form the via holes with high aspect ratio is performed by an RIE technique. Electrical contact between the upper and lower devices is made by filling the via holes 1022 with an electrically conductive material such as tungsten or aluminum.

Figure 14:
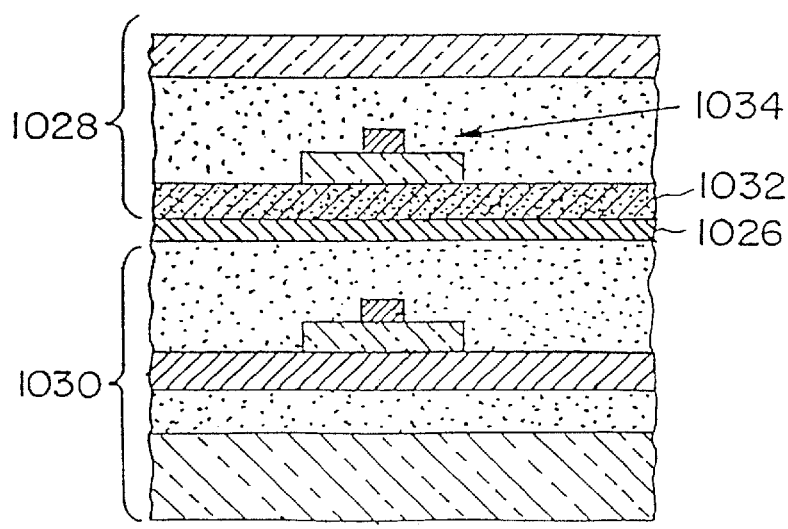
FIG. 14 illustrates a shielding layer positioned in a layered structure for minimizing undesirable electrical interference between layered devices.

Another significant aspect of three-dimensional circuits involves shielding device layers to avoid undesirable electrical interference between devices. Referring to FIG. 14, ground planes 1026 are positioned between device layers 1028 and 1030 to prevent electrical interference. These conductive ground planes 1026 can be made with a metal or by ITO deposition on the surface of the oxide layer 1032 opposite the device 1034. Alternatively, the ground planes can be formed with an electrically conductive epoxy or with a highly doped silicon layer taking the place of a device layer in the stacked structure.

B. 3-D Device Formation

In accordance with the present invention, a fabrication process comprising single and double transfer steps and a backside processing step can be employed to provide various 3-D devices. The fabrication process includes the formation of circuits in a Si film of an SOI structure, adhering the circuits to a superstrate and removal of the substrate. At this point, the silicon circuits have been single-transferred and the backside of the silicon circuit layer is exposed. Backside processing can be performed so long as the processing is compatible with the selected adhesive. After backside processing is performed, the silicon circuit layer is transferred to a glass substrate (double-transfer).

Figure 15A:
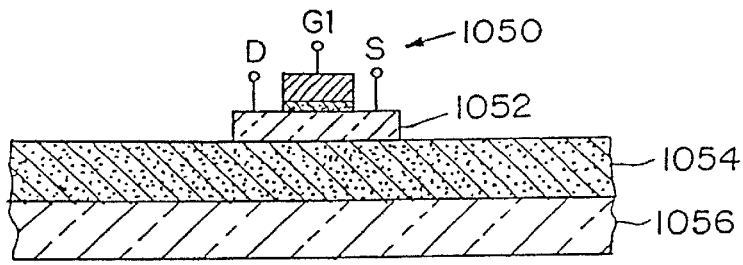
FIGS. 15A–15G is a process flow sequence illustrating the fabrication of a 3-D double gate MOSFET device.
Figure 15B:
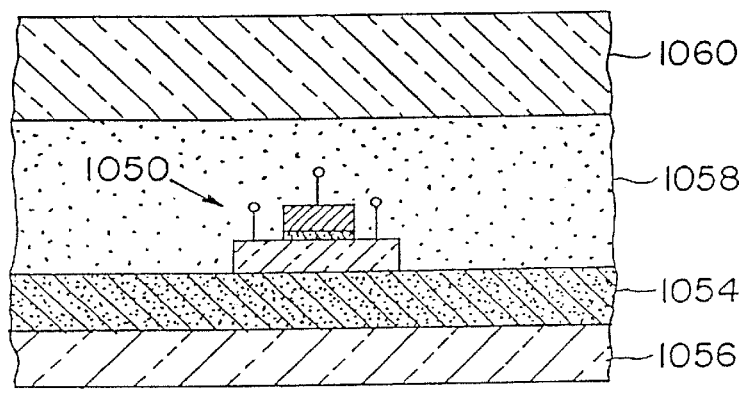
Figure 15C:
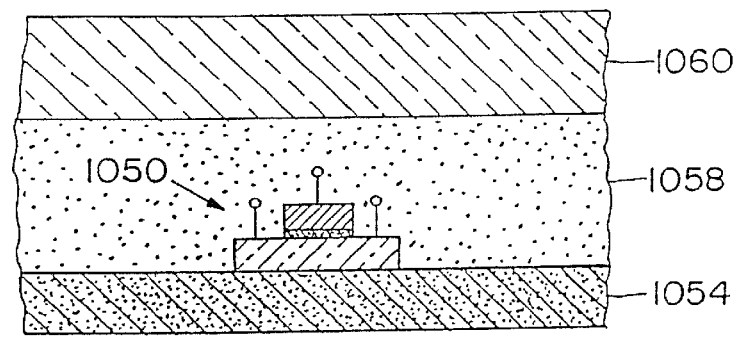
Figure 15D:
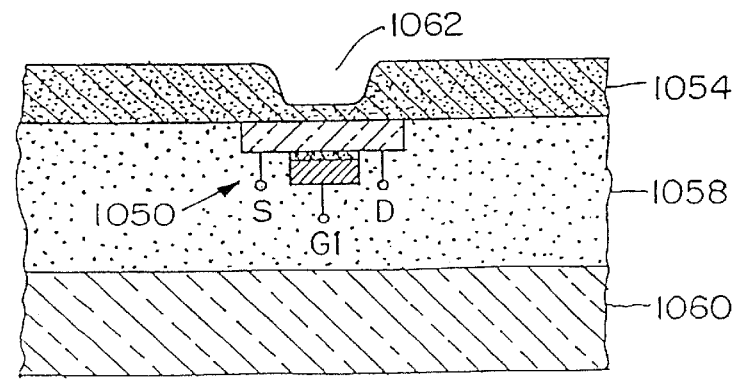

In one preferred embodiment, a double gate MOSFET can be formed in accordance with the above-described fabrication process. First, a standard MOSFET device 1050 having a drain (D), a gate (G1) and a source (S) (FIG. 15A) is formed by an suitable method such as described previously herein. The next step in the process is to transfer the device film 1052 from its substrate 1056 to a superstrate for backside processing. A single transfer approach is shown in FIGS. 15B–15D. Referring to FIG. 15B, an epoxy 1058 is used to attach an optically transmissive superstrate 1060. In a preferred embodiment, a glass superstrate coated with α-Si is employed with a two-part epoxy. Once the front surface of the film 1052 has been bonded to the superstrate 1060, the substrate 1056 is etched off by placing the sample into a 25% KOH solution at ~95° C. As shown in FIG. 15C, the KOH solution rapidly removes the silicon substrate 1056 with the oxide layer 1054 serving as an etch stop. The etch rate selectivity of 200:1 for silicon versus thermal silicon dioxide allows the use of very thin oxide layers leaving the device 1050 protected from the etchant.

Figure 15E:
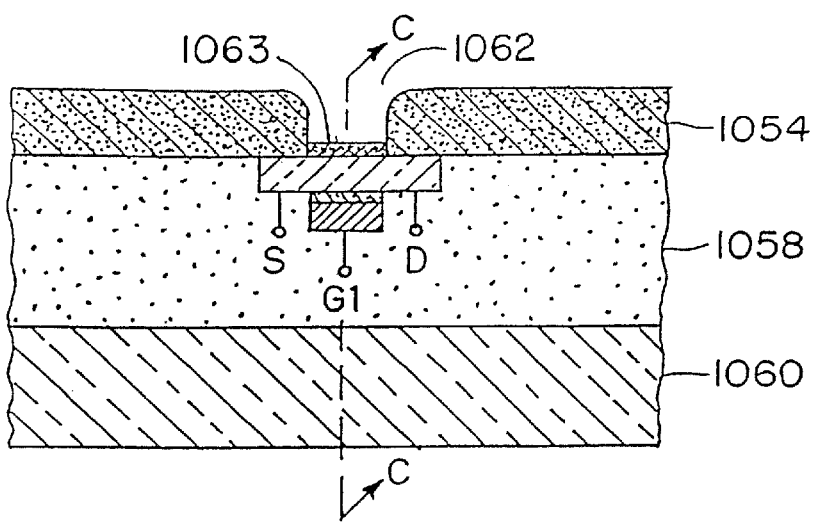

After single transfer, using an opposite polarity gate mask (not shown) the oxide layer 1054 is thinned down to a few hundred angstroms (~500 Å) along the channel region 1062 (FIG. 15D). An alternative method of providing a thin oxide layer adjacent the backside of the MOSFET device 1050 is illustrated in FIG. 15E. Once again using a mask (not shown), the oxide layer along the channel region 1062 is etched away to expose the backside of the device 1050. Next, a thin oxide layer 1063 (~500 Å) can be deposited in the region 1062.

Figure 15F:
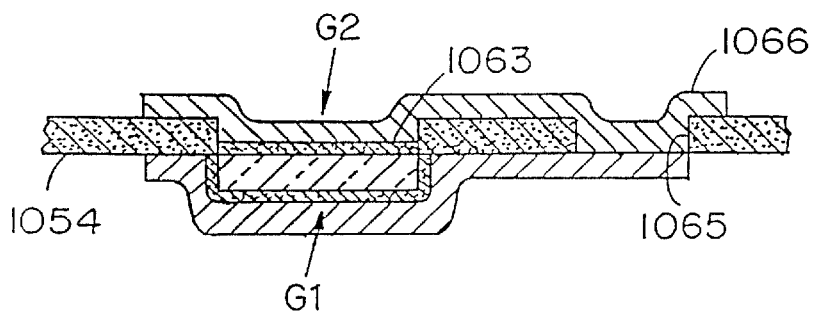
Figure 15G:
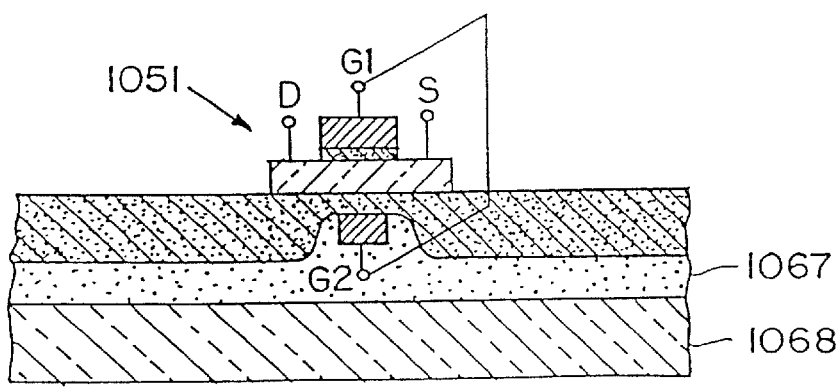

A second gate (G2) is then formed over the thin oxide layer 1063 and electrically connected to the first gate (G1) as follows. Referring to FIG. 15F, which is a cross-sectional view of the structure shown FIG. 15E a contact hole 1065 can be opened through the thinned oxide, and a gate material (1066) can be deposited and etched to form a second gate (G2) 1064 which is electrically connected to the first gate (G1). This dual gate configuration serves to practically double the drive current for the MOSFET 1051 since the device has two channels. Referring to FIG. 15G, the dual gate MOSFET 1051 may be transferred again and bonded with epoxy 1067 to a permanent substrate 1068 such as glass.

Figure 16A:
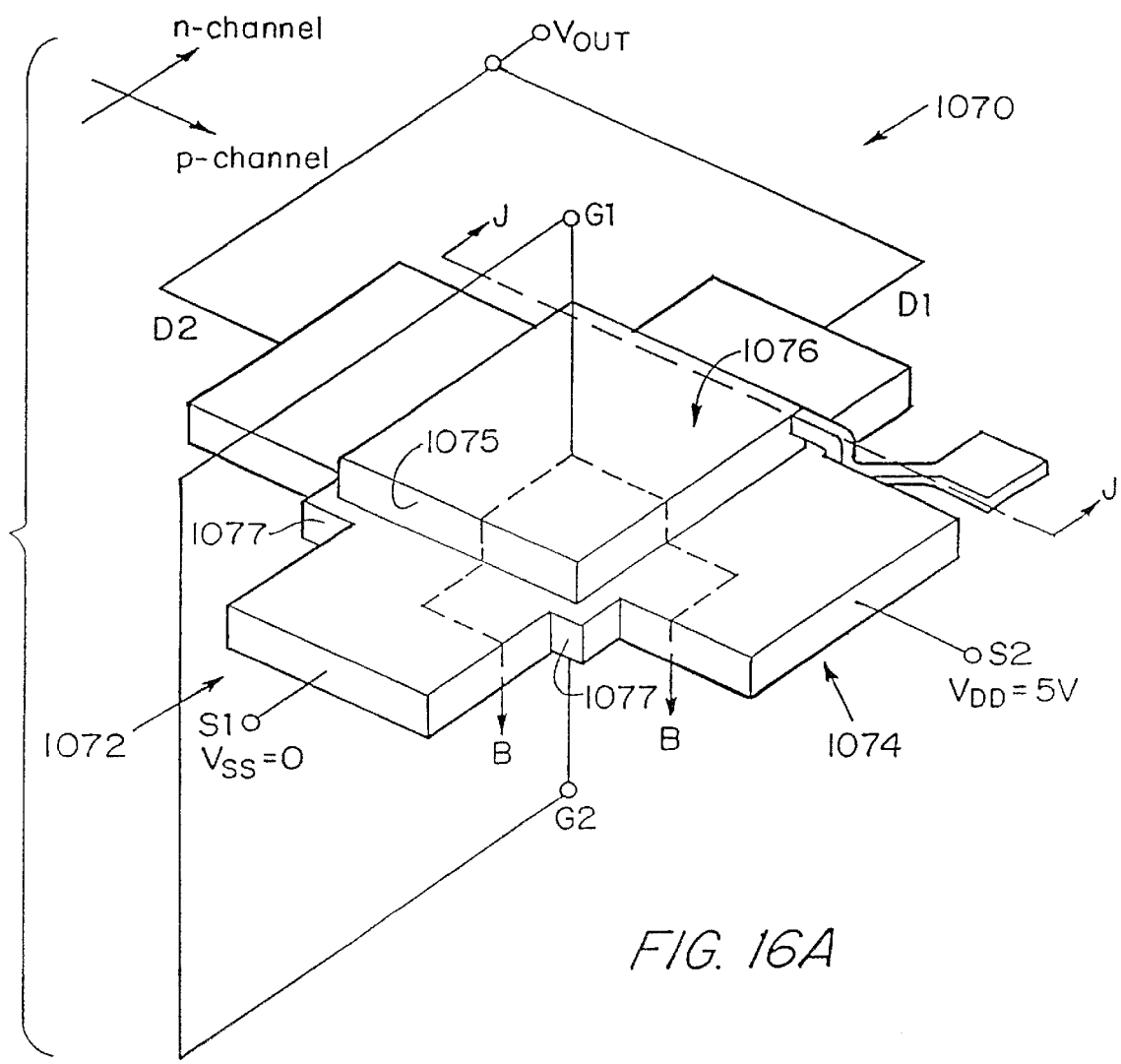
FIGS. 16A–16J is a process flow sequence illustrating the fabrication of a 3-D double gate inverter.
Figure 16B:
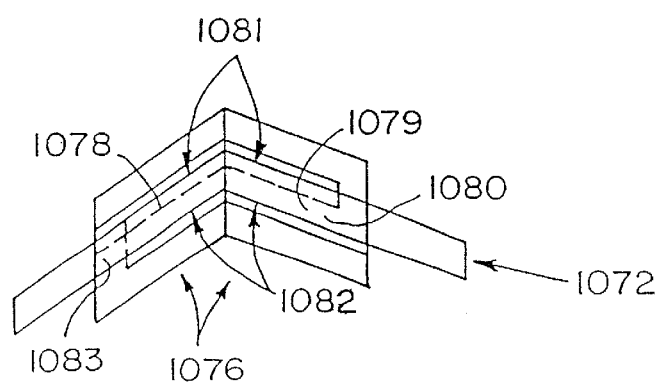

In another preferred embodiment, a 3-D double-gate MOSFET inverter 1070 can be fabricated such that the n-channel and p-channel MOSFETS share the same body with their channels disposed on opposite sides thereof. The fabrication sequence for providing a double-gate inverter is shown in FIGS. 16A–16J. Referring to FIG. 16A, the device 1070 includes an n-channel MOSFET 1072 with a gate (G1), source (S1) and drain (D1) and a p-channel MOSFET 1074 with a gate (G2), source (S2) and a drain (D2). Referring to FIG. 16B, the shared region 1076 includes the n-channel 1078 and the p-channel 1080 which are disposed on opposite sides of the region. More specifically, the channel for the n-channel MOSFET is disposed along the top interface 1081 of the shared region and the channel for the p-channel MOSFET is disposed along the bottom interface 1082 of the shared region.

Figure 16C:
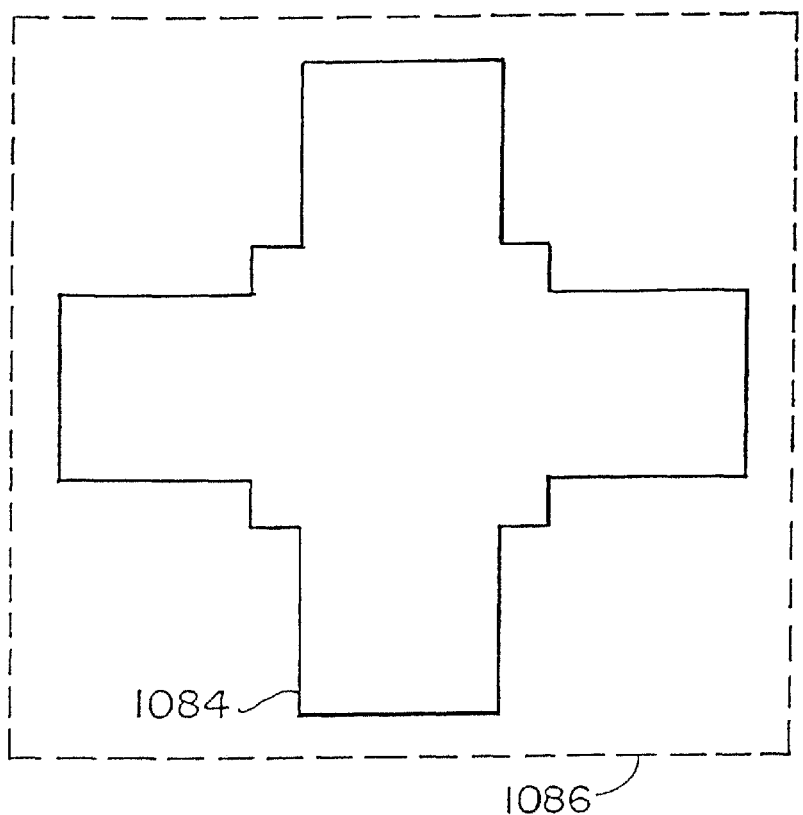
Figure 16D:
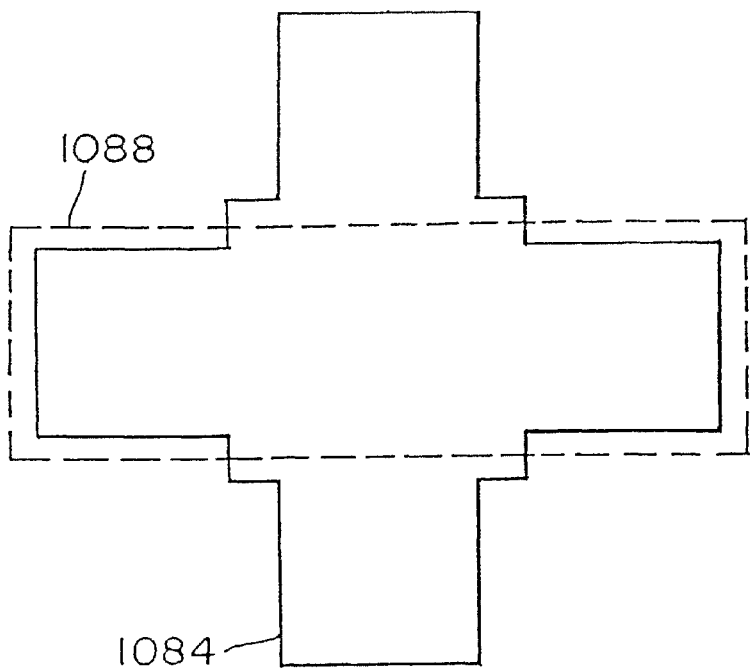

A series of plan views illustrating the processing steps employed for fabricating a double gate MOSFET inverter are shown in FIGS. 16C–16J. FIG. 16C illustrates the channel doping for the p-channel MOSFET. A photoresist and a mask are positioned over the patterned silicon island 1084 and phosphorous (or other n-type dopants) is implanted into the area 1086 with a projected range ($R_p$) near the bottom interface 1082 (FIG. 16B). The implant is such that the phosphorous concentration at the bottom interface is about $10^{16}$ cm$^{-3}$. FIG. 16D illustrates the channel doping for the n-channel MOSFET. Using a photoresist and mask, boron (or other p-type dopants) is implanted in the area 1088 with an $R_p$ near the top interface 1081 (FIG. 16B). The implant preferably produces a boron concentration at the top interface of about $4\times10^{16}$ cm$^{-3}$.

Figure 16E:
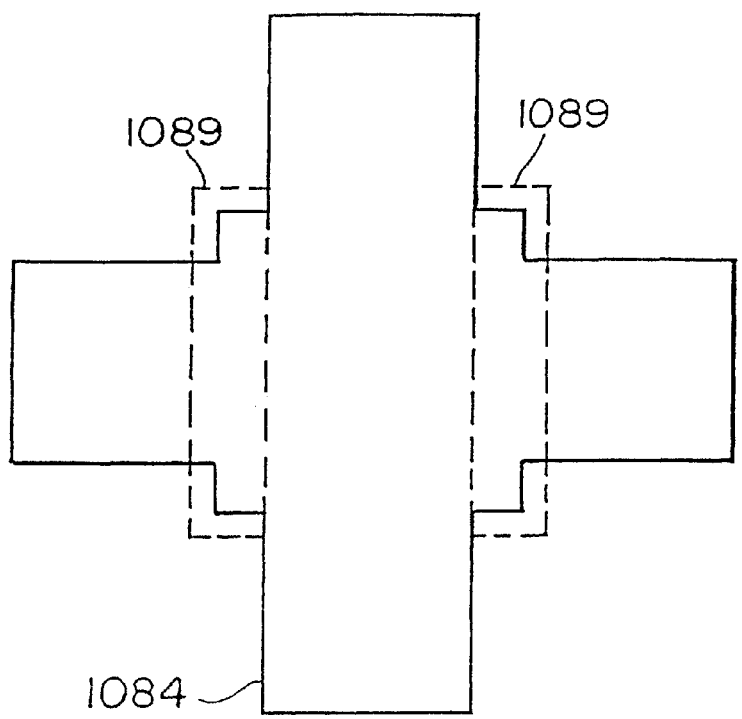
Figure 16F:
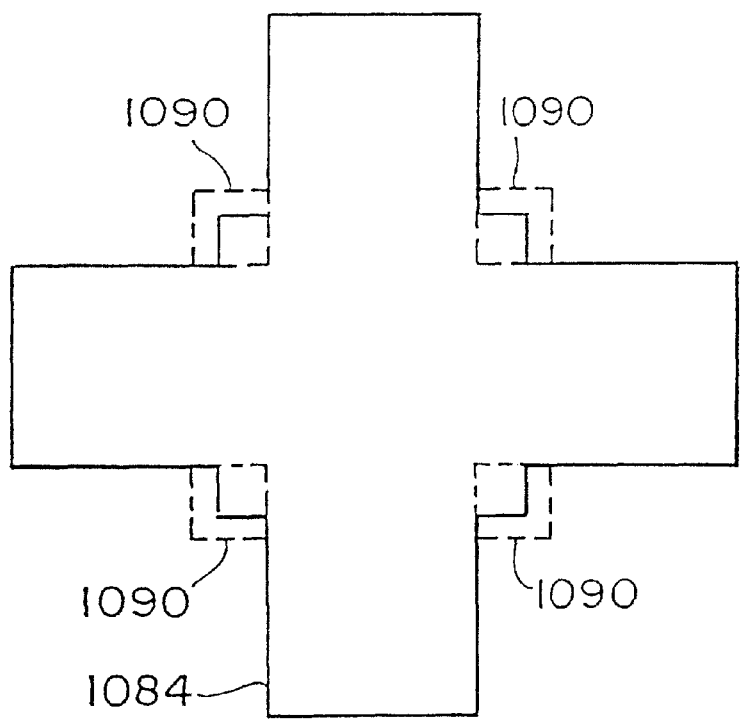

FIG. 16E illustrates the formation of the channel stop 1083 (FIG. 16B) for the n-channel MOSFET. A photoresist and mask are positioned over the silicon island such that boron is implanted into the regions 1089 with an $R_p$ in the in the middle of silicon. This implant is such that the average boron concentration in the middle of the silicon is about $4\times10^{16}$ cm$^{-3}$. FIG. 16F illustrates an edge implant for the n-channel MOSFET. To avoid the effect of sidewall parasitic transistors, the corner regions 1077 (FIG. 16A) extend beyond the gate material preventing the gate from contacting the sidewall of the silicon island to form a sidewall transistor. Further, these corner regions are heavily doped to minimize sidewall transistor effects on the double-gate inverter. Using a photoresist and mask, boron (or other p-type dopant) is implanted into the areas 1090 with an $R_p$ near the top interface. The implant preferably produces a boron concentration at the top interface of about $5\times10^{17}$ cm$^{-3}$.

Figure 16G:
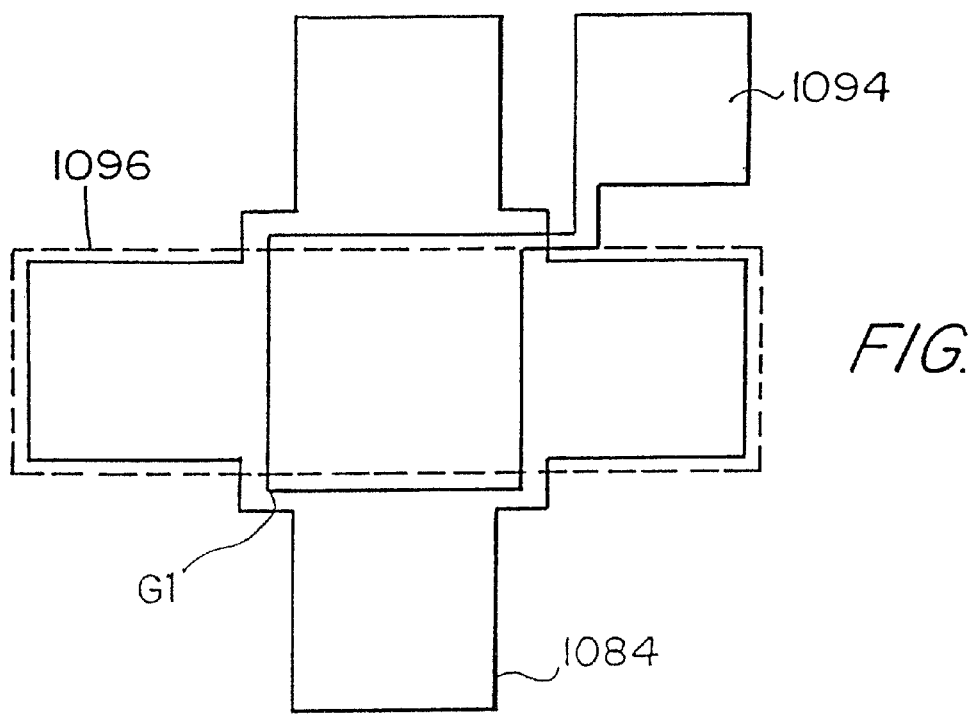
Figure 16H:
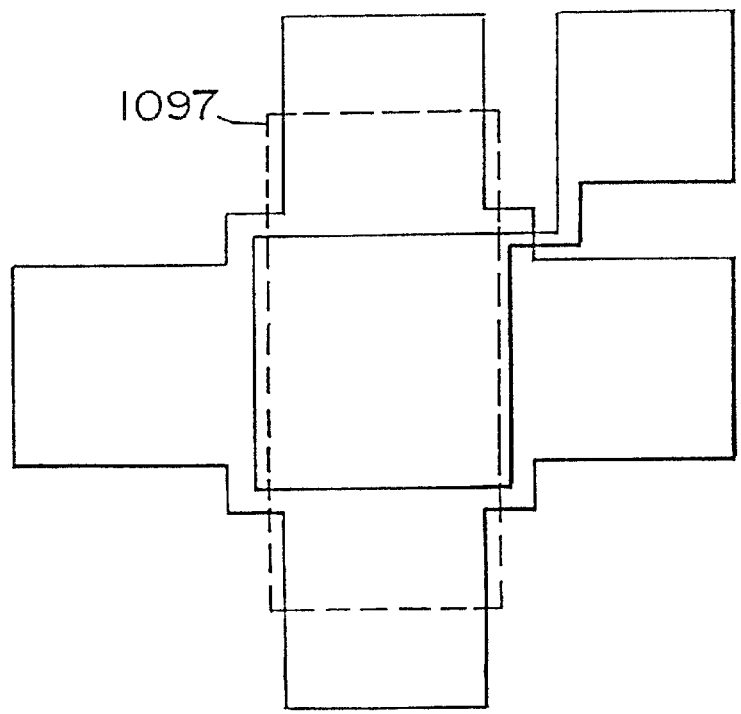
Figure 16I:
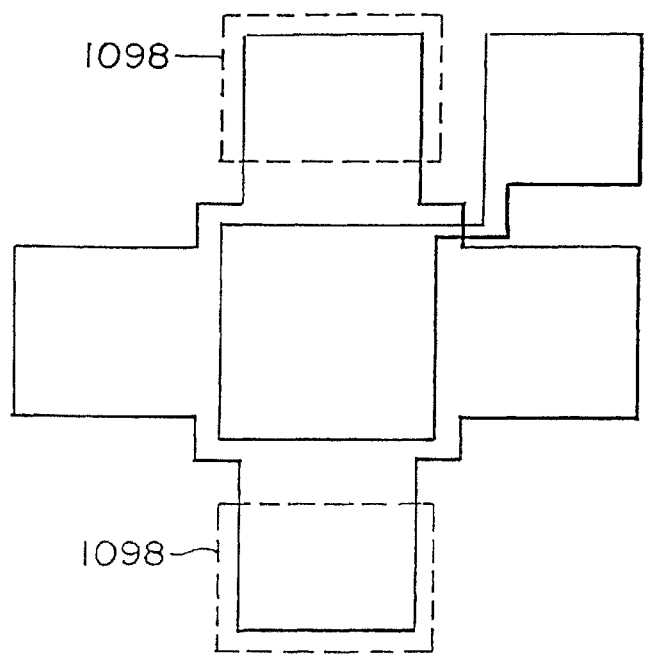

Referring to FIG. 16G, the gate (G1) and the contact area 1094 are then formed for n-channel MOSFET. Next, the source/drain doping is performed for the n-channel device. Using a photoresist and mask, arsenic (or other n-type dopants) is implanted, self-aligned with the gate (G1), into the area 1096 with an $R_p$ near the top interface and an arsenic concentration of about $10^{20}$ cm$^{-3}$. FIG. 16H illustrates the formation of the channel stop 1079 (FIG. 16B) for the p-channel MOSFET. Using a photoresist and mask, phosphorus (or other n-type dopants) is implanted, self-aligned with the gate (G1), into the area 1097 with an $R_p$ near the top interface 1081 (FIG. 16B) and a phosphorus concentration of about $8\times10^{16}$ cm$^{-3}$. Next, the source/drain doping is performed for the p-channel MOSFET. Again using a photoresist and mask, boron is implanted into the areas 1098 with a $R_p$ in the middle of the silicon and an average boron concentration of $10^{20}$ cm$^{-3}$.

Figure 16J:
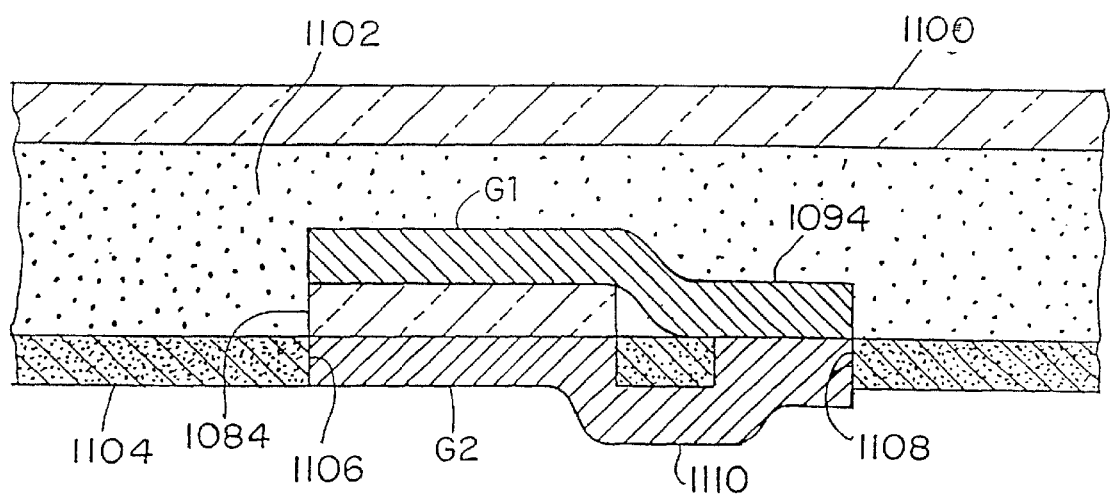

Next, the gate (G2) is formed for the p-channel MOSFET and electrically connected to the gate (G1). Referring to FIG. 16J (which is a sectional view of FIG. 16A taken along the line J—J), the double-gate MOSFET is single transferred to a temporary superstrate 1100 and attached to the superstrate by an adhesive or epoxy 1102. Then, the oxide layer 1104 upon which the device is disposed is selectively etched using a photoresist and a mask to open two areas 1106 and 1108. Next, the gate (G2) is formed in the area 1106 by metalization as well as the contact path 1110 to the contact area 1094. After metallization, the two gates are electrically connected.

Figure 17A:
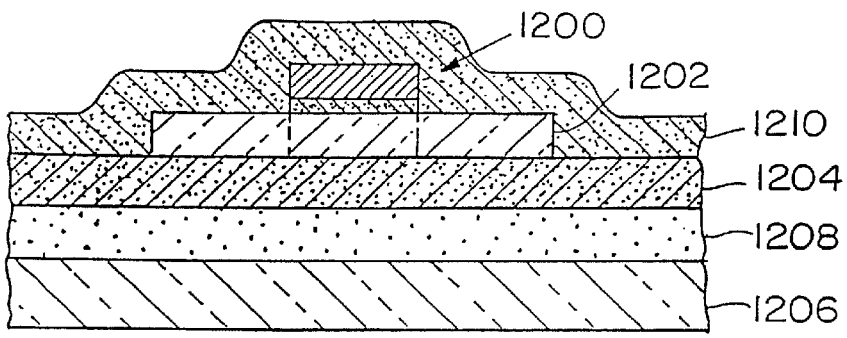
FIGS. 17–17D is a process flow sequence illustrating the fabrication of a 3-D stacked inverter.
Figure 17B:
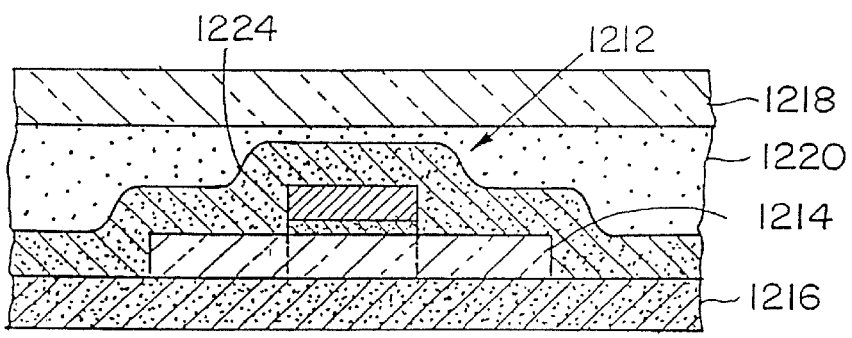
Figure 17C:
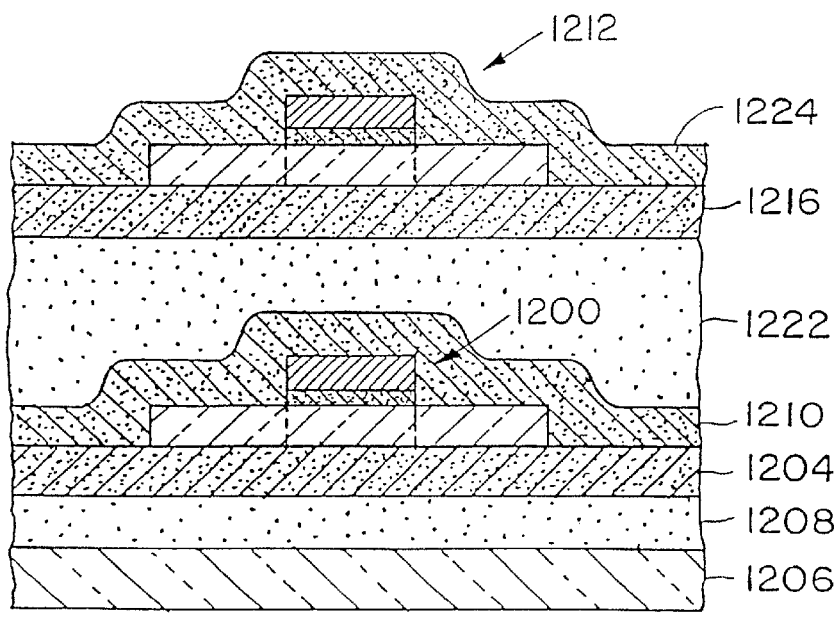
Figure 17D:
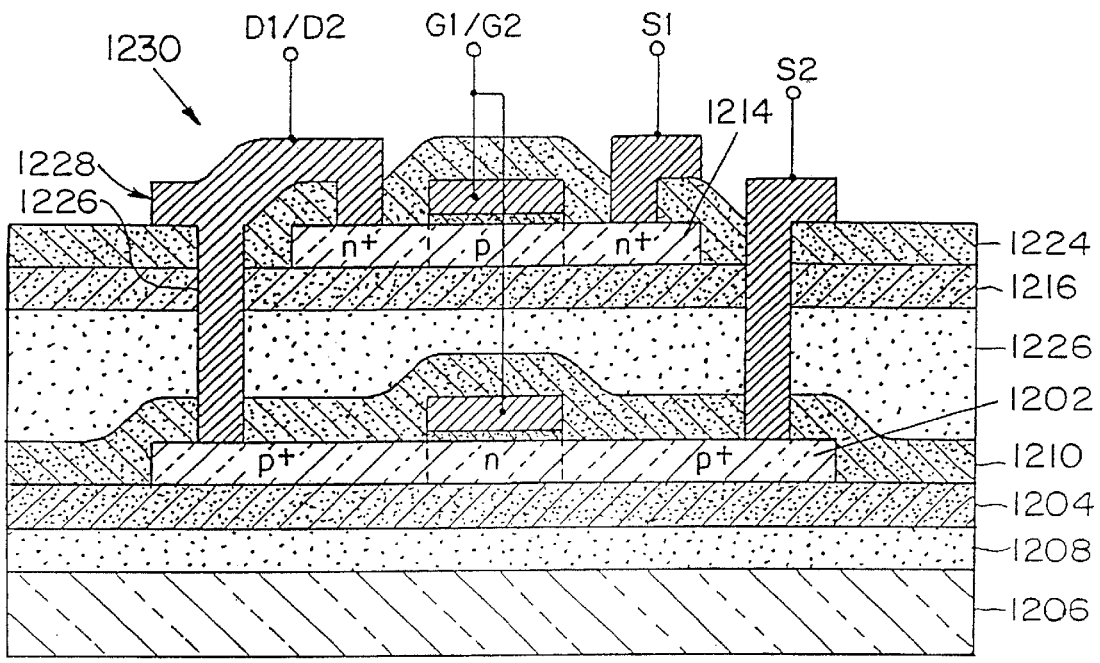

In another preferred embodiment, a three-dimensional inverter, is formed with a pair of MOSFETs which are vertically stacked as shown in FIG. 17D. The fabrication process for the three-dimensional inverter is shown in FIGS. 17A–17D. Referring to FIG. 17A, an n-channel device 1200 is formed in single crystal silicon 1202 on an oxide 1204 over a substrate (not shown). After a double transfer, the device 1200 is attached with an adhesive or epoxy 1208. A passivation oxide layer 1210 is deposited over the device 120.

Referring to FIG. 17B, a p-channel device 1212 is separately fabricated in single crystal silicon 1214 on an oxide 1216 on a substrate (not shown). An oxide layer 1224 is deposited over the p-channel device 1212 for passivation, and single transfer is performed such that the device is attached to a superstrate 1218 by an adhesive 1220. The p-channel device 1212 is then attached to the n-channel device by an adhesive 1222 forming a stacked structure (FIG. 17C).

Next, an oxide layer 1224 is deposited over the p-channel device 1212 for passivation. Referring to FIG. 17D, vias 1226 are then formed to access the gate, source and drain regions of the upper device 1212 and the buried device 1200. A metal layer 1228 is deposited and patterned to form electrical interconnects, for the stacked inverter structure 1230. It is noted that the interconnection of the respective gates is made in a plane parallel to the figure such that the vias are not shown.

Figure 18A:
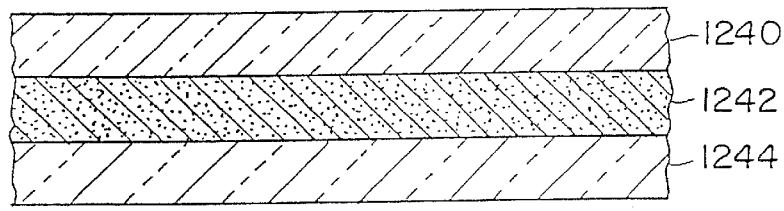
FIGS. 18A–18H is a process flow sequence illustrating the fabrication of a vertical bipolar transistor.
Figure 18B:
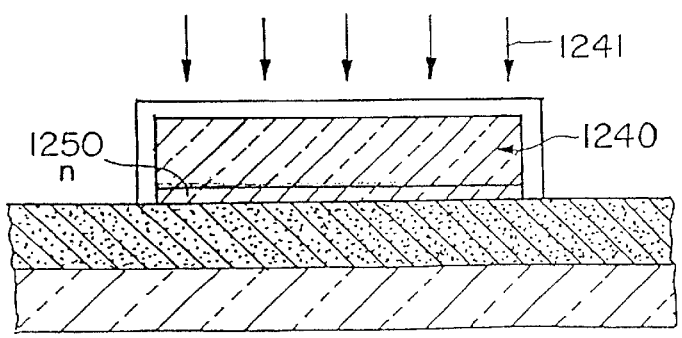
Figure 18C:
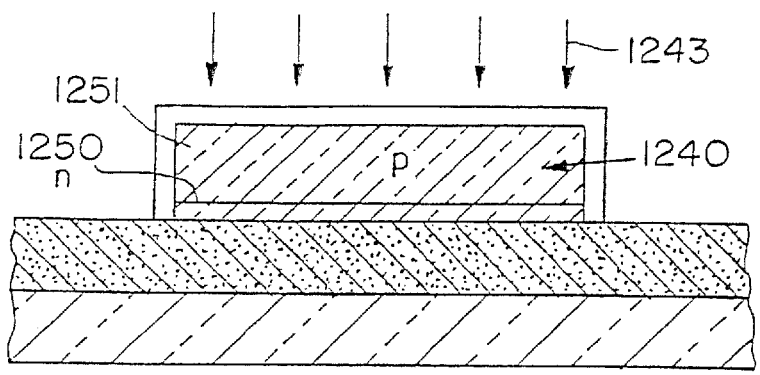
Figure 18D:
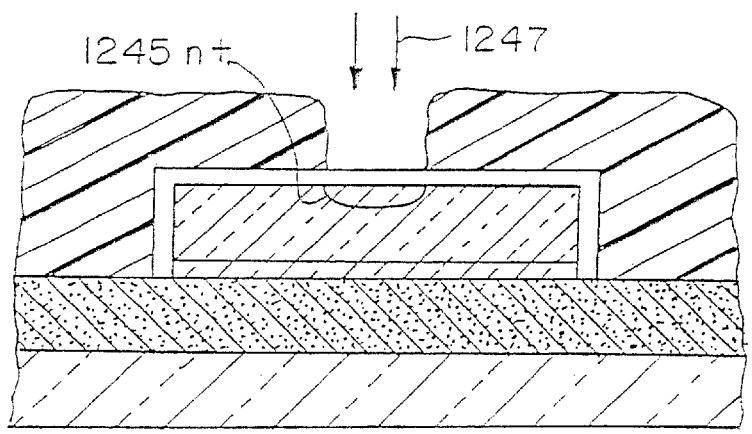
Figure 18E:
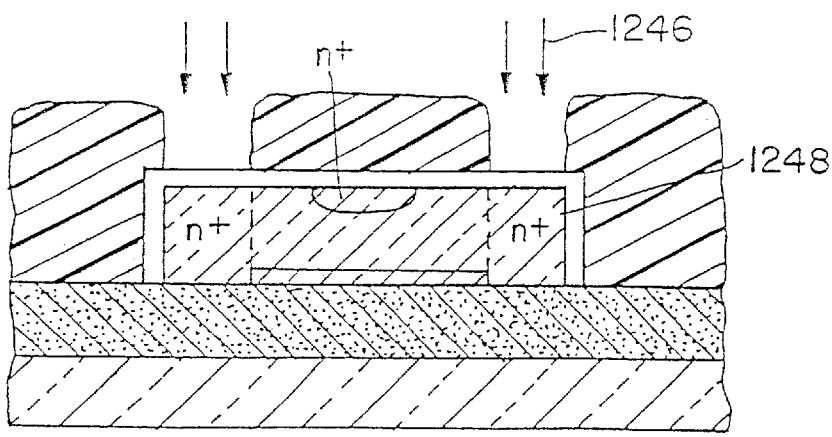
Figure 18F:
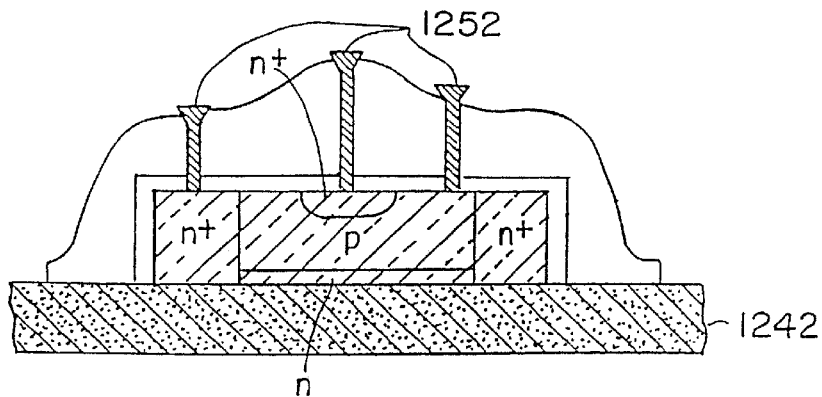

In yet another preferred embodiment, a vertical bipolar transistor is fabricated in accordance with the principles of the present invention. The fabrication process sequence is shown in FIGS. 18A–18H. Beginning with a silicon film 1240 on an oxide 1242 on a substrate 1244 (FIG. 18A), the silicon is patterned into device regions as shown in FIG. 18B. Next, a deep implant of an n-type dopant 1241 is performed for producing an n-doped collector region 1250. Referring to FIG. 18C, the device region is doped with boron or other p-type dopants 1243 for providing a p-type base region 1251. Referring to FIG. 18D, the silicon is doped with an n-type dopant 1244 to provide an n+ emitter region 1245. Next, the silicon is heavily doped with an n-type material 1247 to provide an n+ collector region 1248 (FIG. 18E).

Figure 18G:
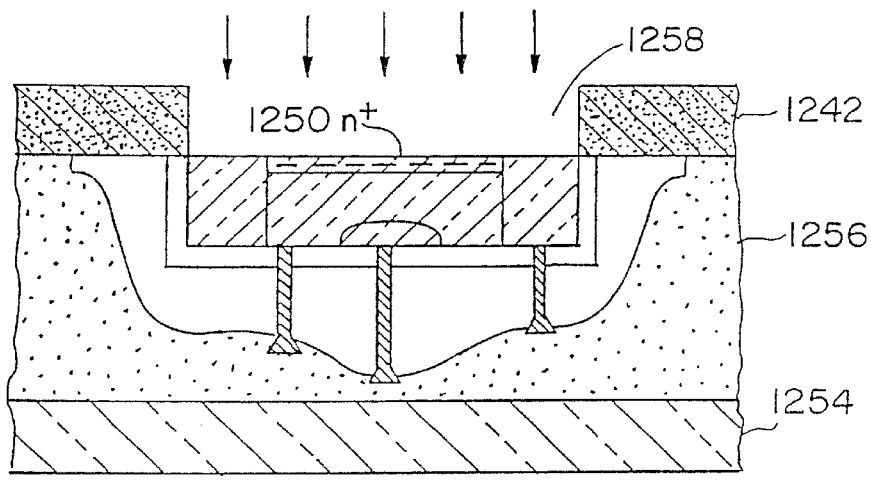
Figure 18H:
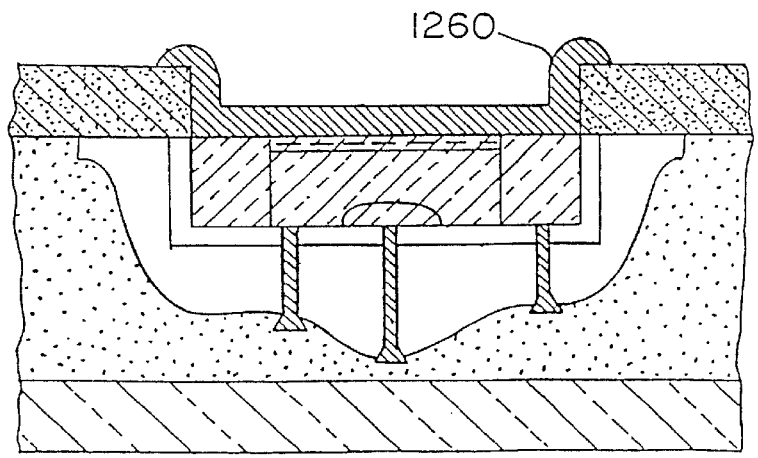

The collector, emitter and base contacts 1252 can be formed (FIG. 18F) and the device can be transferred to a superstrate 1254 (FIG. 18G). The device is attached to the superstrate with an epoxy 1256 and inverted for further processing. To that end, a portion of the oxide layer 1242 is etched forming an opening 1258 at the back of the silicon layer. Next, a metal layer 1260 is applied over the exposed backside of the silicon film and sintered (FIG. 18H). A high temperature implant (~450° C.) can be implemented prior to metalization to produce an n+ buried conductor layer 1250 provided that a high temperature epoxy is used.

Equivalents

While the invention has been particularly shown and described with reference to preferred embodiments thereof, it will be understood by those skilled in the art that various changes in form and details may be made therein without departing form the spirit and scope of the invention as defined by the appended claims.

What is claimed is:

1. A multilayered field effect transistor circuit module device comprising:
    a first circuit layer formed with a first silicon-on-insulator structure, the first circuit layer having a plurality of transistors formed therein;
    a second circuit layer formed with a second silicon-on-insulator structure the second circuit layer having a plurality of transistors formed therein;
    an adhesive layer extending between the first circuit layer and the second circuit layer; and
    a plurality of conductive interconnects extending through the adhesive layer and connecting the first circuit to the second circuit.

2. The device of claim 1 further comprising a plurality of double gated field effect transistors.

3. The device of claim 1 wherein the device comprises an inverter.

4. The device of claim 1 wherein the adhesive comprises a cycloaliphatic anhydride.

5. The device of claim 1 wherein the insulator comprises a silicon oxide layer on a silicon substrate.

6. The device of claim 1 wherein the adhesive comprises a thermally conductive epoxy.

7. The device of claim 1 further comprising a second adhesive layer.

8. The device of claim 2 wherein each double gated field effect transistor comprises a MOSFET having a first gate electrically connected to a second gate.

9. A semiconductor device comprising:
    a single crystal silicon semiconductor layer having a device region;
    a first layer extending over the device region;
    a bonding layer extending over the first layer and the device region such that the bonding layer is separated from the device region by the first layer, the bonding layer bonding the device region to a supporting substrate.

10. The semiconductor device of claim 9 wherein the device region comprises a display circuit.

11. The semiconductor device of claim 9 wherein the semiconductor layer comprises a single crystal thin film layer.

12. The semiconductor device of claim 9 wherein the bonding layer comprises an adhesive layer.

13. The semiconductor device of claim 9 wherein the first layer comprises a passivation layer.

14. The semiconductor device of claim 9 wherein the device comprises a bipolar transistor.

15. The semiconductor device of claim 9 wherein the semiconductor layer comprises a silicon-on-insulator structure.

16. The semiconductor device of claim 9 wherein semiconductor layer is attached to a single crystal silicon substrate.

17. The semiconductor device of claim 9 wherein the supporting substrate comprises a glass substrate.

18. The semiconductor device of claim 9 wherein the bonding layer comprises an epoxy adhesive layer.

19. The semiconductor device of claim 9 wherein the first layer comprises an oxide film.

20. The semiconductor device of claim 9 further comprising an insulated gate field effect transistor having a source region and a drain region formed with the device region, a channel region formed in the semiconductor layer between the source region and the drain region, an insulating film formed over the channel region and a gate electrode formed over the insulating film.

21. The semiconductor device of claim 9 wherein the first layer is formed on the device region such that a circuit element formed on a first surface of the semiconductor layer is covered by the first layer.

22. The semiconductor device of claim 9 further comprising a second semiconductor layer having a second device region, a second layer formed over the second device region being bonded to the first device region with the bonding layer.

23. The semiconductor device of claim 22 wherein the second device region is electrically connected to the first device region through an opening in the bonding layer and the first layer.

24. The semiconductor device of claim 9 further comprising conductive connectors extending through the first layer and the bonding layer.

25. A liquid crystal light valve comprising:
    a semiconductor layer having a device region including a drive circuit and an electrode connected to the drive circuit;
    a first layer extending over the device region;
    a bonding layer extending over the first layer and the device region, the bonding layer bonding the device region to a supporting substrate; and
    a liquid crystal layer positioned between the semiconductor layer and an opposing substrate.

26. The light valve of claim 25 wherein the device region comprises an active matrix display circuit.

27. The light valve of claim 25 wherein the semiconductor layer comprises a single crystal thin film layer.

28. The light valve of claim 25 wherein the bonding layer comprises an adhesive layer.

29. The light valve of claim 25 wherein the first layer comprises a passivation layer.

30. The light valve of claim 25 wherein the semiconductor layer comprises a silicon-on-insulator structure.

31. The light valve of claim 25 wherein semiconductor layer is attached to a single crystal silicon substrate.

32. The light valve of claim 25 wherein the supporting substrate comprises a glass substrate.

33. The light valve of claim 25 wherein the bonding layer comprises an epoxy adhesive layer.

34. The light valve of claim 25 wherein the first layer comprises an oxide film.

35. The light valve of claim 25 further comprising an insulated gate field effect transistor having a source region and a drain region formed with the device region, a channel region formed in the semiconductor layer between the source region and the drain region, an insulating film formed over the channel region and a gate electrode formed over the insulating film.

36. The light valve of claim 25 wherein the first layer is formed on the device region such that a circuit element formed on a first surface of the semiconductor layer is covered by the first layer.

37. The light valve of claim 25 further comprising a plurality of pixel electrodes arranged in a matrix wherein each pixel electrode is actuated by a corresponding pixel circuit.

* * * * *